(12) United States Patent
Bock et al.

(10) Patent No.: US 7,897,723 B2
(45) Date of Patent: Mar. 1, 2011

(54) ERBB RECEPTOR-DERIVED PEPTIDE FRAGMENTS

(75) Inventors: Elisabeth Bock, Charlottenlund (DK); Vladimir Berezin, Copenhagen (DK); Gro Klitgaard Povlsen, Valby (DK)

(73) Assignee: Københavns Universitet, København K (DK)

( * ) Notice: Subject to any disclaimer, the term of this patent is extended or adjusted under 35 U.S.C. 154(b) by 0 days.

(21) Appl. No.: 12/226,091

(22) PCT Filed: Apr. 3, 2007

(86) PCT No.: PCT/DK2007/000171

§ 371 (c)(1), (2), (4) Date: Dec. 3, 2008

(87) PCT Pub. No.: WO2007/115571

PCT Pub. Date: Oct. 18, 2007

(65) Prior Publication Data

US 2009/0092617 A1 Apr. 9, 2009

(30) Foreign Application Priority Data

Apr. 7, 2006 (DK) .............................. 2006 00500

(51) Int. Cl.
*A61K 38/04* (2006.01)
*A61K 38/00* (2006.01)
*A01N 37/18* (2006.01)

(52) U.S. Cl. .................. 530/326; 530/300; 514/1.1; 514/7.6; 514/21.4

(58) Field of Classification Search .................. None
See application file for complete search history.

(56) References Cited

FOREIGN PATENT DOCUMENTS

| EP | 1479693 | 11/2004 |
|---|---|---|
| WO | WO 01/08636 | 2/2001 |
| WO | WO 2006/026569 | 3/2006 |

OTHER PUBLICATIONS

Baselga J, Arteage CL (2005): Critical update and emerging trends in epidermal growth factor receptor targeting in cancer, J Clin Oncol 23 (11), 2445-59.
Bouyan S et al. (2005): The extracellular region of ErbB4 adopts a tethered conformation in the absence of ligand, PNAS, vol. 102, No. 42, 15024-15029.
Brandt R et al. (2000): Mammary gland specific hEGF receptor transgene expression induces neoplasia and inhibits differentiation. Oncogene 19, 2129-37.
Burgess AW et al. (2003): An open-and-shut case? Recent insight into the activation of EGF/ErbB receptors. Molecular Cell, vol. 12, 541-552.
Cho HS et al. (2002): Structure of the extracellular region of HER3 reveals an interdomain tether. Science, 297, 1330-1333.
Cho HS et al. (2003): Structure of the extracellular region of HER2 alone and in complex with the Herceptin Fab. Nature, vol. 421, 756-760.
Citri A et al. (2003): The deaf and the dumb: the biology of ErbB-2 and ErbB-3. Experimental Cell Research, 284, 54-65.
Di Fiore PP et al. (1987a): ErbB2 is a potent oncogene when overexpressed in NIH/3T3 cells. Science, vol. 237, 178-182.
Di Fiore PP et al. (1987b): Overexpression of the human EGF receptor confers an EGF-dependent transformed phenotype to NIH/3T3 cells. Cell, vol. 51, 1063-1070.
Dmytriyev A et al. (2006): An automatic procedure for evaluation of single cell motility, Cytometry Part A , 69A, 979-985.
Ferguson K et al. (2003): EGF activates its receptor by removing interactions that autoinhibit ectodomain dimerisation. Molecular Cell, vol. 11, 507-517.
Franklin MC et al. (2004): Insights into ErbB signaling from the structure of the ErbB-pertuzumab complex. Cancer Cell, vol. 5, 317-328.
Garrett T et al. (2002): Crystal structure of a truncated epidermal growth factor receptor extracellular domain bound to transforming growth factor alfa. Cell, vol. 110, 763-773.
Garrett TP et al. (2003): The crystal structure of a truncated ErbB2 ectodomain reveals an active conformation, poised to interact with other ErbB receptors, Molecular Cell, vol. 11, 495-505.
Graus-Porta D et al. (1997): ErbB-2, the preferred heterodimerization partner of all ErbB receptors, is a mediator of lateral signalling. EMBO Journal, vol. 16, No. 7, 1647-1655.
Guy PM et al. (1994): Insect Cell-Expressed p180erbB3 Possesses an Impaired Tyrosine Kinase Activity. PNAS USA. vol. 91, 8132-8136.
Jorissen R et al. (2003): Epidermal growth factor receptor: mechanisms of activation and signaling. Experimental Cell Research, 284, 31-53.
Krane IM, Leder P (1996): NDF/heregulin induces persistence of terminal end buds and adenocarcinomas in the mammary glands of transgenic mice. Oncogene 12, 1781-8.
Kwok TT, and Sutherland R M (1991): Differences in EGF related radiosensitistion of human squamous carcinoma cells with high and low numbers of EGF receptors. Br J Cancer, 64, 251-254.
Marmor MD et al. (2004): Signal transduction andoncogenesis by ErbB/HER receptors. Int J Radiation Oncology, vol. 58, No. 3, 903-913.
Mattoon D et al. (2004): The tethered configuration of the EGF receptor extracellular domain exerts only a limited control of receptor function. PNAS, vol. 101, 923-928.
Nakamura T, Takasugi H, Aizawa T, Yoshida M, Mizugushi M, Mori Y, Shinoda H, Hayakawa Y, Kawano K (2005): Peptide mimics of epidermal growth factor with antagonistic activity. Journal of Biotechnology, 116, 211-219.

(Continued)

*Primary Examiner*—Olga N Chemyshev
(74) *Attorney, Agent, or Firm*—Weingarten, Schurgin, Gagnebin & Lebovici LLP

(57) ABSTRACT

The invention relates to new peptide compounds capable of modulating cell proliferation, differentiation, survival and/or motility. The peptide compounds of the invention comprise short peptide fragments of the ErbB receptor and are capable of binding to ErbB and modulating activity of the receptor. The invention also relates to antibodies capable of binding to an epitope comprising a peptide sequence of the invention, pharmaceutical compositions comprising the peptide sequences and/or antibodies and uses thereof for treatment of conditions wherein modulating activity of ErbB is needed.

18 Claims, 8 Drawing Sheets

OTHER PUBLICATIONS

Normanno N. et al. (2003): Target-based agents against ErbB receptors and their ligands: a novel approach to cancer treatment. Endocrine-Related Cancer, 10, 1-21.

Normanno N. et al. (2005): The ErbB receptors and their ligands in cancer: an overview. Current Drug Targets, 6, 243-257.

Ogiso H et al. (2002): Crystal structure of the complex of human epidermal growth factor and receptor extracellular domains, Cell, vol. 110, 775-787.

Olayioye MA et al. (2000): The ErbB signalling network: receptor heterodimerzation in development and cancer. EMBO Journal, vol. 19, 3159-3167.

Pero SC et al. (2004): Identification of a small peptide that inhibits the phosphorylation of ErbB2 and proliferation of ErbB2 overexpressing breast cancer cells. Int J Cancer, 111, 951-60.

Schlessinger J (2002): Ligand-induced, receptor-mediated dimerisation and activation of EGF receptor. Cell, vol. 110, 669-672.

Shankar V et al. (1989): Transformation of an established mouse mammary epithelial cell line following transfection with a human transforming growth factor alpha cDNA, Mol Carcinogi 2, 1-11.

Tzahar E et al. (1996): A hierarchical network of interreceptor interactions determines signal transduction by neu differentiation factor/ neuregulin and epidermal growth factor. Molecular and Cellular Biology, vol. 16, No. 10, 5276-5287.

Worthylake R et al. (1999): ErbB-2 amplification inhibits downregulation and induces constitutive activation of both ErbB-2 and epidermal growth factor receptors. Journal of Biological Chemistry, vol. 274, No. 13, 8865-8874.

Xue C et al. (2006): ErbB3-depemdemt motility and intravasation in breast cancer metastasis. Cancer Res, 66 (3) 1418-26.

Yarden Y, Slwkowski M (2001): Untangling the ErbB signalling network. Nature Reviews, vol. 2, 127-137.

SEQUENCE LISTING

```
<160> NUMBER OF SEQ ID NOS: 40

<210> SEQ ID NO 1
<211> LENGTH: 17
<212> TYPE: PRT
<213> ORGANISM: Artificial sequence
<220> FEATURE:
<223> OTHER INFORMATION: Inherbin 1 peptide

<400> SEQUENCE: 1

Met Leu Tyr Asn Pro Thr Thr Tyr Gln Met Asp Val Asn Pro Glu Gly
1               5                   10                  15

Lys

<210> SEQ ID NO 2
<211> LENGTH: 17
<212> TYPE: PRT
<213> ORGANISM: Artificial sequence
<220> FEATURE:
<223> OTHER INFORMATION: Inherbin 2 peptide

<400> SEQUENCE: 2

Val Thr Tyr Asn Thr Asp Thr Phe Glu Ser Met Pro Asn Pro Glu Gly
1               5                   10                  15
```

-continued

Arg

<210> SEQ ID NO 3
<211> LENGTH: 17
<212> TYPE: PRT
<213> ORGANISM: Artificial sequence
<220> FEATURE:
<223> OTHER INFORMATION: Inherbin 3 peptide

<400> SEQUENCE: 3

Leu Val Tyr Asn Lys Leu Thr Phe Gln Leu Glu Pro Asn Pro His Thr
1               5                   10                  15

Lys

<210> SEQ ID NO 4
<211> LENGTH: 17
<212> TYPE: PRT
<213> ORGANISM: Artificial sequence
<220> FEATURE:
<223> OTHER INFORMATION: Inherbin 4 peptide

<400> SEQUENCE: 4

Phe Val Tyr Asn Pro Thr Thr Phe Gln Leu Glu Met Asn Phe Asn Ala
1               5                   10                  15

Lys

<210> SEQ ID NO 5
<211> LENGTH: 17
<212> TYPE: PRT
<213> ORGANISM: Artificial sequence
<220> FEATURE:
<223> OTHER INFORMATION: Mouse ErbB2dl peptide

<400> SEQUENCE: 5

Ile Thr Tyr Asn Thr Asp Thr Phe Glu Ser Met Leu Asn Pro Glu Gly
1               5                   10                  15

Arg

<210> SEQ ID NO 6
<211> LENGTH: 17
<212> TYPE: PRT
<213> ORGANISM: Artificial sequence
<220> FEATURE:
<223> OTHER INFORMATION: Mouse ErbB3dl peptide

<400> SEQUENCE: 6

Leu Val Tyr Asn Lys Leu Thr Phe Gln Leu Glu Pro Asn Pro His Ile
1               5                   10                  15

Lys

<210> SEQ ID NO 7
<211> LENGTH: 10
<212> TYPE: PRT
<213> ORGANISM: Artificial sequence
<220> FEATURE:
<223> OTHER INFORMATION: AUER1c peptide

<400> SEQUENCE: 7

Ala Gly Val Met Gly Glu Asn Asn Thr Leu
1               5                   10

<210> SEQ ID NO 8
<211> LENGTH: 10
<212> TYPE: PRT

<213> ORGANISM: Artificial sequence
<220> FEATURE:
<223> OTHER INFORMATION: Mouse AUER1c peptide

<400> SEQUENCE: 8

Ala Gly Ile Met Gly Glu Asn Asn Thr Leu
1               5                   10

<210> SEQ ID NO 9
<211> LENGTH: 12
<212> TYPE: PRT
<213> ORGANISM: Artificial sequence
<220> FEATURE:
<223> OTHER INFORMATION: AUER1n peptide

<400> SEQUENCE: 9

Ala His Tyr Ile Asp Gly Pro His Ser Val Lys Thr
1               5                   10

<210> SEQ ID NO 10
<211> LENGTH: 10
<212> TYPE: PRT
<213> ORGANISM: Artificial sequence
<220> FEATURE:
<223> OTHER INFORMATION: AUER2c peptide

<400> SEQUENCE: 10

Ser Gly Val Lys Pro Asp Leu Ser Tyr Met
1               5                   10

<210> SEQ ID NO 11
<211> LENGTH: 12
<212> TYPE: PRT
<213> ORGANISM: Artificial sequence
<220> FEATURE:
<223> OTHER INFORMATION: AUER2n peptide

<400> SEQUENCE: 11

Ala His Tyr Lys Asp Pro Pro Phe Ser Val Ala Arg
1               5                   10

<210> SEQ ID NO 12
<211> LENGTH: 12
<212> TYPE: PRT
<213> ORGANISM: Artificial sequence
<220> FEATURE:
<223> OTHER INFORMATION: Mouse AUER2n peptide

<400> SEQUENCE: 12

Ala His Tyr Lys Asp Ser Ser Ser Cys Val Ala Arg
1               5                   10

<210> SEQ ID NO 13
<211> LENGTH: 10
<212> TYPE: PRT
<213> ORGANISM: Artificial sequence
<220> FEATURE:
<223> OTHER INFORMATION: AUER3c peptide

<400> SEQUENCE: 13

His Gly Val Leu Gly Ala Lys Gly Pro Ile
1               5                   10

<210> SEQ ID NO 14
<211> LENGTH: 10
<212> TYPE: PRT
<213> ORGANISM: Artificial sequence

```
<220> FEATURE:
<223> OTHER INFORMATION: Mouse AUER3c peptide

<400> SEQUENCE: 14

His Gly Ile Leu Gly Ala Lys Gly Pro Ile
1               5                   10

<210> SEQ ID NO 15
<211> LENGTH: 12
<212> TYPE: PRT
<213> ORGANISM: Artificial sequence
<220> FEATURE:
<223> OTHER INFORMATION: AUER3n peptide

<400> SEQUENCE: 15

Ala His Phe Arg Asp Gly Pro His Ser Val Ser Ser
1               5                   10

<210> SEQ ID NO 16
<211> LENGTH: 12
<212> TYPE: PRT
<213> ORGANISM: Artificial sequence
<220> FEATURE:
<223> OTHER INFORMATION: Mouse AUER3n peptide

<400> SEQUENCE: 16

Ala His Phe Arg Asp Gly Pro His Cys Val Asn Ser
1               5                   10

<210> SEQ ID NO 17
<211> LENGTH: 10
<212> TYPE: PRT
<213> ORGANISM: Artificial sequence
<220> FEATURE:
<223> OTHER INFORMATION: AUER4c peptide

<400> SEQUENCE: 17

Asp Gly Leu Gln Gly Ala Asn Ser Phe Ile
1               5                   10

<210> SEQ ID NO 18
<211> LENGTH: 12
<212> TYPE: PRT
<213> ORGANISM: Artificial sequence
<220> FEATURE:
<223> OTHER INFORMATION: AUER4n peptide

<400> SEQUENCE: 18

Ser His Phe Lys Asp Gly Pro Asn Ser Val Glu Lys
1               5                   10

<210> SEQ ID NO 19
<211> LENGTH: 13
<212> TYPE: PRT
<213> ORGANISM: Artificial sequence
<220> FEATURE:
<223> OTHER INFORMATION: InhB2_1 peptide

<400> SEQUENCE: 19

Gly Leu Pro Arg Glu Tyr Val Asn Ala Arg His Cys Leu
1               5                   10

<210> SEQ ID NO 20
<211> LENGTH: 13
<212> TYPE: PRT
<213> ORGANISM: Artificial sequence
<220> FEATURE:
```

```
<223> OTHER INFORMATION: Mouse InhB2_1 peptide

<400> SEQUENCE: 20

Gly Leu Pro Arg Glu Tyr Val Arg Gly Lys His Cys Leu
1               5                   10

<210> SEQ ID NO 21
<211> LENGTH: 12
<212> TYPE: PRT
<213> ORGANISM: Artificial sequence
<220> FEATURE:
<223> OTHER INFORMATION: InhB2_2 peptide

<400> SEQUENCE: 21

His Pro Glu Cys Gln Pro Gln Asn Gly Ser Val Thr
1               5                   10

<210> SEQ ID NO 22
<211> LENGTH: 12
<212> TYPE: PRT
<213> ORGANISM: Artificial sequence
<220> FEATURE:
<223> OTHER INFORMATION: Mouse InhB2_2 peptide

<400> SEQUENCE: 22

His Pro Glu Cys Gln Pro Gln Asn Ser Ser Glu Thr
1               5                   10

<210> SEQ ID NO 23
<211> LENGTH: 10
<212> TYPE: PRT
<213> ORGANISM: Artificial sequence
<220> FEATURE:
<223> OTHER INFORMATION: InhB2_3 peptide

<400> SEQUENCE: 23

Phe Gly Pro Glu Ala Asp Gln Cys Val Ala
1               5                   10

<210> SEQ ID NO 24
<211> LENGTH: 10
<212> TYPE: PRT
<213> ORGANISM: Artificial sequence
<220> FEATURE:
<223> OTHER INFORMATION: Mouse InhB2_3 peptide

<400> SEQUENCE: 24

Tyr Gly Ser Glu Ala Asp Gln Cys Glu Ala
1               5                   10

<210> SEQ ID NO 25
<211> LENGTH: 11
<212> TYPE: PRT
<213> ORGANISM: Artificial sequence
<220> FEATURE:
<223> OTHER INFORMATION: InhB2_4 peptide

<400> SEQUENCE: 25

His Tyr Lys Asp Pro Pro Phe Cys Val Ala Arg
1               5                   10

<210> SEQ ID NO 26
<211> LENGTH: 11
<212> TYPE: PRT
<213> ORGANISM: Artificial sequence
<220> FEATURE:
<223> OTHER INFORMATION: Mouse InhB2_4 peptide
```

```
<400> SEQUENCE: 26

His Tyr Lys Asp Ser Ser Ser Cys Val Ala Arg
1               5                   10

<210> SEQ ID NO 27
<211> LENGTH: 8
<212> TYPE: PRT
<213> ORGANISM: Artificial sequence
<220> FEATURE:
<223> OTHER INFORMATION: InhB2_5 peptide

<400> SEQUENCE: 27

Ser Gly Val Lys Pro Asp Leu Ser
1               5

<210> SEQ ID NO 28
<211> LENGTH: 13
<212> TYPE: PRT
<213> ORGANISM: Artificial sequence
<220> FEATURE:
<223> OTHER INFORMATION: InhB2_6 peptide

<400> SEQUENCE: 28

Tyr Met Pro Ile Trp Lys Phe Pro Asp Glu Glu Gly Ala
1               5                   10

<210> SEQ ID NO 29
<211> LENGTH: 13
<212> TYPE: PRT
<213> ORGANISM: Artificial sequence
<220> FEATURE:
<223> OTHER INFORMATION: Mouse InhB2_6 peptide

<400> SEQUENCE: 29

Tyr Met Pro Ile Trp Lys Tyr Pro Asp Glu Glu Gly Ile
1               5                   10

<210> SEQ ID NO 30
<211> LENGTH: 8
<212> TYPE: PRT
<213> ORGANISM: Artificial sequence
<220> FEATURE:
<223> OTHER INFORMATION: B1dln peptide

<400> SEQUENCE: 30

Leu Met Leu Tyr Asn Pro Thr Thr
1               5

<210> SEQ ID NO 31
<211> LENGTH: 7
<212> TYPE: PRT
<213> ORGANISM: Artificial sequence
<220> FEATURE:
<223> OTHER INFORMATION: B1dlc peptide

<400> SEQUENCE: 31

Thr Tyr Gln Met Asp Val Asn
1               5

<210> SEQ ID NO 32
<211> LENGTH: 7
<212> TYPE: PRT
<213> ORGANISM: Artificial sequence
<220> FEATURE:
<223> OTHER INFORMATION: B2dln peptide
```

-continued

```
<400> SEQUENCE: 32

Leu Val Thr Tyr Asn Thr Asp
1               5

<210> SEQ ID NO 33
<211> LENGTH: 7
<212> TYPE: PRT
<213> ORGANISM: Artificial sequence
<220> FEATURE:
<223> OTHER INFORMATION: Mouse B2dln peptide

<400> SEQUENCE: 33

Leu Ile Thr Tyr Asn Thr Asp
1               5

<210> SEQ ID NO 34
<211> LENGTH: 7
<212> TYPE: PRT
<213> ORGANISM: Artificial sequence
<220> FEATURE:
<223> OTHER INFORMATION: B2dlc peptide

<400> SEQUENCE: 34

Thr Phe Glu Ser Met Pro Asn
1               5

<210> SEQ ID NO 35
<211> LENGTH: 7
<212> TYPE: PRT
<213> ORGANISM: Artificial sequence
<220> FEATURE:
<223> OTHER INFORMATION: Mouse B2dlc peptide

<400> SEQUENCE: 35

Thr Phe Glu Ser Met Leu Asn
1               5

<210> SEQ ID NO 36
<211> LENGTH: 8
<212> TYPE: PRT
<213> ORGANISM: Artificial sequence
<220> FEATURE:
<223> OTHER INFORMATION: B3dln peptide

<400> SEQUENCE: 36

Pro Leu Val Tyr Asn Lys Leu Thr
1               5

<210> SEQ ID NO 37
<211> LENGTH: 7
<212> TYPE: PRT
<213> ORGANISM: Artificial sequence
<220> FEATURE:
<223> OTHER INFORMATION: B3dlc peptide

<400> SEQUENCE: 37

Thr Phe Gln Leu Glu Pro Asn
1               5

<210> SEQ ID NO 38
<211> LENGTH: 7
<212> TYPE: PRT
<213> ORGANISM: Artificial sequence
<220> FEATURE:
<223> OTHER INFORMATION: B4dln peptide

<400> SEQUENCE: 38
```

```
Thr Phe Val Tyr Asn Pro Thr
1               5

<210> SEQ ID NO 39
<211> LENGTH: 7
<212> TYPE: PRT
<213> ORGANISM: Artificial sequence
<220> FEATURE:
<223> OTHER INFORMATION: B4d1c peptide

<400> SEQUENCE: 39

Thr Phe Gln Leu Glu Met Asn
1               5

<210> SEQ ID NO 40
<211> LENGTH: 17
<212> TYPE: PRT
<213> ORGANISM: Artificial sequence
<220> FEATURE:
<223> OTHER INFORMATION: Scr-Inherbin3d peptide

<400> SEQUENCE: 40

Lys His Lys Leu Pro Tyr Asn Phe Asn Leu Glu Thr Thr Val Gln Pro
1               5                   10                  15

Leu
```

ERBB RECEPTOR-DERIVED PEPTIDE FRAGMENTS

This application is a §371 national phase filing of PCT/DK2007/000171 filed Apr. 3, 2007; and claims priority to Denmark Application No. PA 2006 00500 filed Apr. 7, 2006.

FIELD OF INVENTION

The invention relates to new peptide compounds capable of modulating cell proliferation, differentiation, survival and/or motility. The peptide compounds of the invention comprise short peptide fragments of the ErbB receptor and are capable of binding to ErbB and modulating activity of the receptor. The invention also relates to antibodies capable of binding to an epitope comprising a peptide sequence of the invention, pharmaceutical compositions comprising the peptide sequences and/or antibodies and uses thereof for treatment of conditions wherein modulating activity of ErbB is needed.

BACKGROUND OF INVENTION

The ErbB Receptor Family and its Ligands

The ErbB family of receptor tyrosine kinases couples binding of extracellular growth factor ligands to intracellular signalling pathways regulating diverse biological responses, including proliferation, differentiation, cell motility, and survival. The four closely related members of this family—ErbB1 (also known as the epidermal growth factor receptor (EGFR)/HER1), ErbB2 (neu, HER2), ErbB3 (HER3), and ErbB4 (HER4)—are activated upon ligand-induced receptor homo- and heterodimerisation. ErbB2 appears to be the preferred heterodimerisation partner for all other ErbB receptors (Tzahar et al., 1996; Graus-Porta et al., 1997).

ErbB ligands are characterised by the presence of an EGF-like domain, and can be divided into three groups on the basis of their specificity towards the ErbB receptors (Normanno et al., 2005): The first group (including EGF, TGFα and amphiregulin) binds specifically to ErbB1, the second group (including betacellulin, heparin-binding EGF, epiregulin), show dual specificity towards ErbB1 and ErbB4, whereas the third group (including the neuregulins (NRGs)) bind ErbB3 and/or ErbB4. None of the EGF-related growth factors bind ErbB2.

ErbB receptors have a broad expression pattern on epithelial, mesenchymal and neuronal cells, and signalling through these receptors plays a critical developmental role in cell fate determination in many organs (Normanno et al., 2005).

Structure and Mechanism of Activation of the ErbB Receptors

All four ErbB receptors have an extracellular ligand-binding domain, a single transmembrane domain and a cytoplasmic tyrosine kinase-containing domain. The intracellular tyrosine kinase domain of ErbB receptors is highly conserved, although the kinase domain of ErbB3 contains substitutions of critical amino acids and therefore lacks kinase activity (Guy et al., 1994). Ligand-induced dimerisation of the ErbB receptors induces activation of the kinase, receptor transphosphorylation on tyrosine residues in the C-terminal tail, followed by recruitment and activation of intracellular signalling effectors (Yarden and Sliwkowski, 2001; Jorissen et al., 2003).

The crystal structures of the extracellular domains of all four ErbBs have provided detailed insight into the process of ligand-induced receptor activation (Schlessinger, 2002). The extracellular domain of each ErbB receptor consists of four subdomains: Subdomain I and III cooperate in forming the ligand-binding site, whereas subdomain II (and perhaps also subdomain IV) participates in receptor dimerisation via direct receptor-receptor interactions. In the structures of ligand-bound ErbB1, a β hairpin (termed the dimerisation loop) in subdomain II penetrates into the dimer partner and stabilises the receptor dimer (Garrett et al., 2002; Ogiso et al., 2002). In contrast, in the structures of the inactive ErbB1, ErbB3 and ErbB4, the dimerisation loop is engaged in intramolecular interactions with subdomain IV, which prevents spontaneous receptor dimerisation in the absence of ligand (Cho and Leahy, 2002; Ferguson et al., 2003; Bouyan et al., 2005). The structure of ErbB2 is unique among the ErbBs. In the absence of a ligand, ErbB2 has a conformation that resembles the ligand-activated state of ErbB1 with a protruding dimerisation loop, poised to interact with other ErbB receptors (Cho et al., 2003; Garrett et al., 2003). This may explain the enhanced heterodimerisation capacity of ErbB2.

Although the ErbB receptor crystal structures provide a model for ErbB receptor homo- and heterodimerisation, the background for the prevalence of some ErbB homo- and heterodimers over others (Franklin et al., 2004) as well as the role of domain IV in receptor dimerisation and autoinhibition (Burgess et al., 2003; Mattoon et al., 2004) remains somewhat unclear.

The Role of ErbB Receptors in Cancer

The role of ErbB receptors in cancer is, particularly for ErbB1 and ErbB2, well documented and characterised by two main lines of evidence: Firstly, the ErbB receptors and their ligands are transforming genes in vitro and in vivo with ErbB2 showing the highest transforming potential (Di Fiore et al., 1987a, b; Shankar et al., 1989; Krane and Leder, 1996; Brandt et al., 2000; Normanno et al., 2005).

Secondly, one or more of the ErbB receptors and/or their ligands are overexpressed in the majority of solid neoplasms (for review, see Marmor et al., 2004; Normanno et al., 2005). As regards ErbB1, overexpression, gene amplification, rearrangements, or mutations of this receptor are found in multiple human malignancies, including cancers of the breast, head and neck, and lung. Accumulating evidence suggest that when ErbB1 is overexpressed, the resultant cell transformation is ligand-dependent, and several tumors show overexpression of ErbB1 together with one of its ligands, EGF or TGFα. Mutations of ErbB2 have been found only rarely, if at all, in human tumors. However, ErbB2 is frequently overexpressed in many cancers (most frequently in breast and ovarian tumors), and its overexpression is associated with poor prognosis. ErbB2 overexpression triggers spontaneous homo- and/or heterodimer formation and ligand-independent activation of the kinase domain.

Co-expression of different ErbB receptors occurs in the majority of carcinomas, and tumors that co-express different ErbB receptors are often associated with a more aggressive phenotype and a worse clinical outcome (Olayioye et al., 2000). Especially, co-expression of ErbB2 confers increased transforming potential to the other ErbB receptors, due to the fact that ErbB2-containing heterodimers show increased ligand-binding affinities, evade ligand-induced receptor downregulation and are more biologically potent (Worthylake et al., 1999; Olayioye et al., 2000). In fact, consensus is emerging that heterodimers of the ligand-less ErbB2 and the kinase-defective ErbB3 provide the most potent mitogenic and metastatic ErbB signal (Olayioye et al., 2000; Citri et al., 2003; Xue et al., 2006).

ErbB Receptor-Targeted Cancer Therapy

Due to the pivotal role of the ErbB receptors in cancer development, they are obvious targets for cancer therapy.

Several anti-cancer agents targeting the ErbBs are in clinical use or development (for review, see Normanno et al., 2003; Baselga and Arteaga, 2005). They can be divided into two categories:

1. Chimeric or humanised monoclonal antibodies against the ErbB family.

These include antibodies that prevent ligand-binding and ligand-dependent receptor activation (e.g. Cetuximab that targets the ligand-binding subdomain III of ErbB1), antibodies that interfere with ligand-independent receptor activation (e.g. Trastuzumab that targets subdomain IV of ErbB2), and antibodies that prevent receptor heterodimerisation (e.g. the anti-ErbB2 antibody Pertuzumab that targets an area around the dimerisation loop in subdomain II of ErbB2). Cetuximab is approved for the treatment of advanced-stage colorectal cancer, and is being tested in phase III trials for the treatment of squamous cell carcinomas of the head and neck and non-small cell lung cancer. Trastuzumab is approved for the treatment of metastatic breast cancers overexpressing ErbB2, and Pertuzumab in being tested in clinical phase II for the treatment of breast, ovarian, prostate and non-small cell lung cancer. However, there are limitations to the use of ErbB-targeted antibodies. For Trastuzumab, for example, the objective response rates are relatively low, and the majority of patients that benefit from Trastuzumab treatment acquire resistance within one year of treatment initiation.

2. Small Molecule ErbB Tyrosine Kinase Inhibitors.

The two ErbB1-specific tyrosine kinase inhibitors Gefitinib/Iressa and Erlotinib have been approved for the treatment of non-small cell lung cancer, and the dual ErbB1/ErbB2 inhibitors Lapatinib is in phase III trial for the treatment of breast cancer.

As an alternative to the antibody-based strategy of ErbB targeting, two recent studies have attempted to target the ErbB1 and ErbB2 by means of small peptides. The authors identified peptides, which exhibited homology to EGF-like growth factors, and which bound the ligand-binding site in ErbB1 (Nakamura et al., 2005), or an unspecified site in the extracellular domain of ErbB2 (Pero et al., 2004) thereby inhibiting ErbB1- and ErbB2-mediated mitogenesis, respectively. However, there are no reports on attempts to develop peptides that target other extracellular parts of the ErbB receptors (such as the parts involved in receptor dimerisation) and/or peptides that are capable of targeting several ErbB receptors expressed in the same tumor.

REFERENCES

Baselga J, Arteage C L (2005): Critical update and emerging trends in epidermal growth factor receptor targeting in cancer, *J Clin Oncol* 23, 2445-59.

Bouyan S, Lomgo P, Li S, Ferguson K, Leahy D (2005): The extracellular region of ErbB4 adopts a tethered conformation in the absence of ligand, *PNAS* 102, 15024-15029.

Brandt R, Eisenbrandt R, Leenders F, Zschiesche W, Binas B, Juergensen C, Theuring F (2000): Mammary gland specific hEGF receptor transgene expression induces neoplasia and inhibits differentiation, *Oncogene* 19, 2129-37.

Burgess A W, Cho H S, Eigenbrot C, Ferguson K M, Garrett T P, Leahy D J, Lemmon M, Sliwkowski M, Ward C W, Yokoyama S (2003): An open-and-shut case? Recent insight into the activation of EGF/ErbB receptors, *Mol Cell* 12, 541-552.

Cho H S, Leahy D J (2002): Structure of the extracellular region of HER3 reveals an interdomain tether, *Science* 297, 1330-1333.

Cho H S, Mason K, Ramyar K X, Stanley A M, Gabelli S B, Denney D W, Leahy D J (2003): Structure of the extracellular region of HER2 alone and in complex with the Herceptin Fab, *Nature* 421, 756-760.

Citri, Skaria K B, Yarden Y (2003): The deaf and the dumb: the biology of ErbB-2 and ErbB-3. *Exp Cell Res* 284, 54-65

Di Fiore P P, Pierce J H, Kraus M H, Segatto O, King C R, Aronson S A (1987a): ErbB2 is a potent oncogene when overexpressed in NIH/3T3 cells, *Science I* 237, 178-182.

Di Fiore P P, Pierce J H, Kraus M H, Segatto O, King C R, Aronson S A (1987b): Overexpression of the human EGF receptor confers an EGF-dependent transformed phenotype to NIH/3T3 cells, *Cell* 51, 1063-1070.

Dmytriyev A, Tkach V, Rudenko O, Bock E, Berezin V (2066): An automatic procedure for evaluation of single cell motility, *Cytometry A* 69, 979-985.

Ferguson K, Berger M, Mendrola J, Cho H S, Leahy D, Lemmon M (2003): EGF activates its receptor by removing interactions that autoinhibit ectodomain dimerisation, *Mol Cell* 11, 507-517.

Franklin M C, Carey K D, Vajdos F, Leahy D J, de Vos A, Sliwkowski M (2004): Insights into ErbB signaling from the structure of the ErbB-pertuzumab complex, *Cancer Cell* 5, 317-328.

Garrett T, McKern N, Lou M, Elleman T, Adams T, Lovrecz G, Zhu H J, Walker F, Frenkel M, Hoyne P, Jorissen R, Nice E, Burgess A, Ward C (2002): Crystal structure of a truncated epidermal growth factor receptor extracellular domain bound to transforming growth factor α, *Cell* 110, 763-773.

Garrett T P, McKern N M, Lou M, Elleman T C, Adams T E, Lovrecz G O, Kofler M, Jorissen R N, Nice E C, Burgess A W, Ward C W (2003): The crystal structure of a truncated ErbB2 ectodomain reveals an active conformation, poised to interact with other ErbB receptors, *Mol Cell* 11, 495-505.

Graus-Porta D, Beerli R R, Daly J M, Hynes N E (1997): ErbB-2, the preferred heterodimerization partner of all ErbB receptors, is a mediator of lateral signalling, *EMBO J* 16, 1647-1655.

Guy P M, Platko J V, Cantley L C, Cerione R A, Carraway K I (1994): Insect Cell-Expressed p180erbB3 Possesses an Impaired Tyrosine Kinase Activity, *PNAS* 91, 8132-8136.

Jorissen R, Walker F, Pouliot N, Garrett T, Ward C, Burgess A (2003): Epidermal growth factor receptor: mechanisms of activation and signaling, *Exp Cell Res* 284, 31-53.

Krane I M, Leder P (1996): NDF/heregulin induces persistence of terminal end buds and adenocarcinomas in the mammary glands of transgenic mice, *Oncogene* 12, 1781-8.

Kwok T T, and Sutherland R M (1991): Differences in EGF related radiosensitisation of human squamous carcinoma cells with high and low numbers of EGF receptors. *Br J Cancer* 64, 251-254.

Marmor M D, Skaria K B, Yarden Y (2004): Signal transduction andoncogenesis by ErbB/HER receptors, *Int J Rad Oncol* 58, 903-913.

Mattoon D, Klein P, Lemmon M A, Lax I, Schlessinger J (2004): The tethered configuration of the EGF receptor extracellular domain exerts only a limited control of receptor function, *PNAS* 101, 923-928.

Nakamura T, Takasugi H, Aizawa T, Yoshida M, Mizugushi M, Mori Y, Shinoda H, Hayakawa Y, Kawano K (2005):

Peptide mimics of epidermal growth factor with antagonistic activity, *J Biotecnol* 116, 211-219.

Normanno N, Bianco C, De Luca A, Maiello M R, Salomon D S (2003): Target-based agents against ErbB receptors and their ligands: a novel approach to cancer treatment, *Endoc Rel Canc* 10, 1-21.

Normanno N, Bianco C, Strizzi L, Maiello M R, De Luca A, Caponigro F, Salomon D S (2005): The ErbB receptors and their ligands in cancer: an overview. *Curr Drug Targets* 6, 243-257.

Ogiso H, Ishitani R, Nureki O, Fukai S, Yamanaka M, Kim J H, Saito K, Sakamoto A, Inoue M, Shirouzu M, Yokoyama S (2002): Crystal structure of the complex of human epidermal growth factor and receptor extracellular domains, *Cell* 110, 775-787.

Olayioye M A, Neve R M, Lane H A, Hynes N E (2000): The ErbB signalling network: receptor heterodimerzation in development and cancer. *EMBO J.* 19, 3159-3167.

Pero S C, Shukla G S, Armstrong A L, Peterson D, Fuller S P, Godin K, Kingsley-Richards S L, Weaver D L, Bond J, Krag D N (2004): Identification of a small peptide that inhibits the phosphorylation of ErbB2 and proliferation of ErbB2 overexpressing breast cancer cells, *Int J Cancer* 111, 951-60.

Schlessinger J (2002): Ligand-induced, receptor-mediated dimerisation and activation of EGF receptor, *Cell* 110, 669-672.

Shankar V, Ciardiello F, Kim N, Derynck R, Liscia D S, Merlo G, Langton B C, Sheer D, Callahan R, Bassin R H (1989): Transformation of an established mouse mammary epithelial cell line following transfection with a human transforming growth factor alpha cDNA, *Mol Carcinogi* 2, 1-11.

Tzahar E, Waterman H, Chen X, Levkowitz G, Karunagaran D, Lavi S, Ratzkin B J, Yarden Y (1996): A hierarchical network of interreceptor interactions determines signal transduction by neu differentiation factor/neuregulin and epidermal growth factor, *Mol Cell Biol* 16, 5276-5287.

Worthylake R, Opresko L K, Wiley S (1999): ErbB-2 amplification inhibits down-regulation and induces constitutive activation of both ErbB-2 and epidermal growth factor receptors, *J Biol Chem* 274, 8865-8874.

Xue C, Liang F, Mahmood R, Vuolo M, Wyckoff J, Qian H, Tsai K L, Kim M, Locker J, Zhang Z Y, Segali J (2006): ErbB3-dependent motility and intravasation in breast cancer metastasis, *Cancer Res* 66, 1418-26.

Yarden Y, Slwkowski M (2001): Untangling the ErbB signalling network, *Nature Rev* 2, 127-137.

Kwok, T. T., and Sutherland, R. M. (1991) Differences in EGF related radiosensitisation of human squamous carcinoma cells with high and low numbers of EGF receptors. *Br J Cancer* 64, 251-4.

SUMMARY OF INVENTION

The present invention relates to an isolated peptide of at most 30 amino acid residues comprising an amino acid sequence of 6 to 18 amino acid residues, wherein said amino acid sequence is identical or homologous to a subsequence of the polypeptide of the ErbB receptor. A peptide comprising such amino acid sequence is according to the invention capable of i) binding to the ErbB receptor; ii) modulating cell proliferation; iii) modulating cell motility; iii) modulating cell survival; iv) modulating cell differentiation; v) modulating activity of the ErbB receptor.

Accordingly, another aspect of the invention relates to use of peptides of the invention and/or compounds comprising thereof as medicaments and for the preparation of medicaments for treatment of a condition or disease wherein i) modulating cell proliferation, ii) modulating cell motility, iii) modulating cell survival, iv) modulating cell differentiation or v) modulating activity of the ErbB receptor is part of said treatment.

Still, in another aspect a peptide of the invention or a compound comprising the peptide may be used for the production of an antibody.

The invention further relates to pharmaceutical compositions comprising a peptide of the invention, compound comprising thereof or antibody capable of recognising an epitope comprising the peptide.

The invention also concerns a method of treatment of conditions wherein i) modulating cell proliferation, ii) modulating cell motility, iii) modulating cell survival, iv) modulating cell differentiation or v) modulating activity of the ErbB receptor is beneficial, said method comprising a step of administering a peptide sequence of the invention, compound of the invention, antibody of the invention or a pharmaceutical composition comprising said peptide sequence, said compound or said antibody to an individual in need.

DETAILED DESCRIPTION OF THE INVENTION

Figure 1:
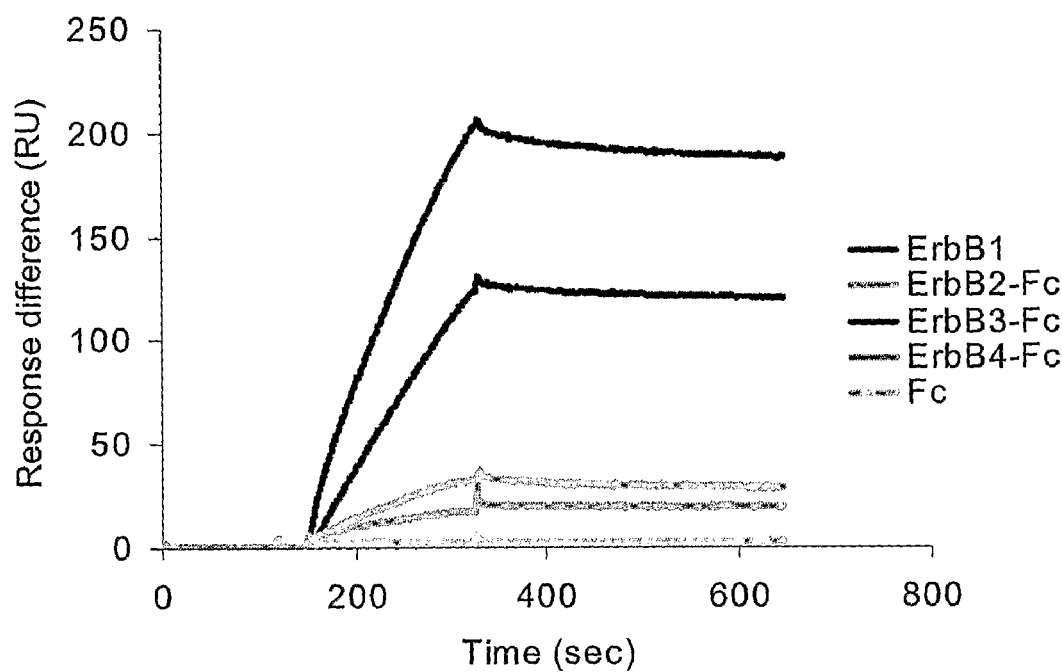
FIG. 1: Binding of Inherbin3 to ErbB receptors. Inherbin3d peptide was immobilized on the sensor surface chip, and recombinant proteins comprising the extracellular parts of the four ErbB receptors were injected and sent floating over the sensor chip surface at concentrations of 64 $\mu$M (for the monomeric ErbB1 protein) and 32 $\mu$M (for the dimeric ErbB2-, ErbB3-, and ErbB4-Fc chimeric proteins). The binding is given as the response difference between the binding to the sensor chip with the immobilized peptide and a blank sensor chip. Shown are representative curves from one of three independent experiments.

1. Peptide Sequence Comprising a Fragment of the ErbB Receptor

In a first aspect the invention relates to an isolated peptide of at most 30 amino acid residues comprising an amino acid sequence of 6 to 18 amino acid residues which is identical or homologous to a subsequence of the polypeptide sequence of a ErbB receptor.

By the term "isolated peptide" is meant that the amino acid sequence of the peptide, which is identical or homologous to a subsequence of a longer polypeptide sequence, represents a separate physical entity and is not a subsequence of a longer polypeptide sequence, e.g. the ErbB receptor or a large fragment of the ErbB receptor.

The invention preferably relates to the isolated peptide comprising a sequence of 6 to 18 amino acid residues, wherein said amino acid sequence is identical or homologous to a subsequence of the polypeptide of the ErbB receptor. By the term "identical" is meant that the isolated peptide may comprise or consists of a sequence of 6 to 18 amino acid residues which represent a fragment of the ErbB receptor comprising 6 to 18 amino acid residues. By the term "homologous" is meant that the isolated peptide may comprise or consists of a sequence of 6 to 18 amino acid residues which is homologous to a subsequence of the ErbB receptor. The homology of one amino acid sequence to another amino acid is defined as a percentage of identical or similar amino acids in two collated sequences. By term "similar amino acids" is meant that two compared amino acid residues in the collated sequences belong to the same group of amino acids (see below). The wording "sequence homology" is used herein synonymously with the term "sequence similarity". The sequence homology is calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90.

A preferred length of a peptide of the invention is at most 30 amino acid residues. The peptide may also be of more than 30 amino acid residues. Such embodiments relate to peptides of at most 50 amino acid residues.

Thus, in one embodiment the peptide of the invention comprises or consists of an amino acid sequence of 6 to 18 amino acid residues which is identical to a subsequence of the ErbB receptor. Such amino acid sequence is also identified and referred herein as a fragment of the ErbB receptor.

Thus, the invention relates to a fragment of the ErbB receptor which consists of at least 6 and most 18 contiguous amino acid residues, such as 7, 8, 9, 10, 11, 12, 13, 14, 15, 16 or 17 amino acid residues.

The ErbB fragment may be a fragment of any receptor belonging to the ErbB family, e.g. a fragment of ErbB1, ErbB2, ErbB3 or ErbB4, such the receptors identified in the GenBank under Ass. Nos.: P00533, NP_004439, P70424, P21860, Q61526, Q15303, NP_997538.

The amino acid sequence comprised by an isolated peptide of the invention may represent a subsequence of any structural domain of any of the above identified ErbB receptors. Preferred peptides of the invention comprise ErbB peptide fragments which represent subsequences of the following structural domains of the ErbB receptor: the dimerisation loop, autoinhibitory loop or membrane proximal domain.

Non-limited examples of amino acid sequences which represent isolated peptide fragments of the ErbB receptor which may be comprised by a peptide of the invention are the amino acid sequences set forth in SEQ ID NOs:1-39. It may also be a fragment or variant of said sequences.

The invention relates to naturally occurring, synthetically prepared or recombinant fragments of the ErbB of above, and fragments prepared by means of enzymatic/chemical cleavage of the polypeptides of the ErbB receptor.

When in the present application is referred to an amino acid sequence the standard one-letter code for amino acid residues is applied as well as the standard three-letter code. Abbreviations for amino acids are in accordance with the recommendations in the IUPAC-IUB Joint Commission on Biochemical Nomenclature Eur. J. Biochem, 1984, vol. 184, pp 9-37. Throughout the description and claims either the three letter code or the one letter code for natural amino acids are used. Where the L or D form has not been specified it is to be understood that the amino acid in question has the natural L form, cf. Pure & Appl. Chem. Vol. (56(5) pp 595-624 (1984) or the D form, so that the peptides formed may be constituted of amino acids of L form, D form, or a sequence of mixed L forms and D forms.

Where nothing is specified it is to be understood that the C-terminal amino acid of a peptide of the invention exists as the free carboxylic acid, this may also be specified as "—OH". However, the C-terminal amino acid of a compound of the invention may be the amidated derivative, which is indicated as "—NH$_2$". Where nothing else is stated the N-terminal amino acid of a polypeptide comprise a free amino-group, this may also be specified as "H—".

Where nothing else is specified amino acid can be selected from any amino acid, whether naturally occurring or not, such as alfa amino acids, beta amino acids, and/or gamma amino acids. Accordingly, the group comprises but are not limited to: Ala, Val, Leu, Ile, Pro, Phe, Trp, Met, Gly, Ser, Thr, Cys, Tyr, Asn, Gln, Asp, Glu, Lys, Arg, His Aib, NaI, Sar, Orn, Lysine analogues, DAP, DAPA and 4Hyp.

Also, according to the invention modifications of the compounds/peptides may be performed, such as for example glycosylation and/or acetylation and/or phosphorylation of the amino acids.

Basic amino acid residues are according to invention represented by the residues of amino acids Arg, Lys, and His, acidic amino acid residues—by the residues of amino acids Glu and Asp. Basic and acidic amino acid residues constitute a group of charged amino acid residues. The group of hydrophobic amino acid residues is represented by the residues of amino acids Leu, Ile, Val, Phe, Trp, Tyr, Met, Ala and Pro.

Thus, in one embodiment the peptide may comprise or consists of an amino acid sequence selected from SEQ ID NOs:1-29. In another embodiment the peptide may comprise or consists of a fragment or variant of said sequence. The amino acid sequence may be present in the peptide as a single copy, i.e. formulated as a monomer of the peptide sequence, or it may be present as several copies of the same sequence, e.g. as a multimer comprising two or more copies of a sequence selected from SEQ ID NOs:1-29, or two or more copies of a fragment or a variant of said sequence. Other types of multimeric presentation of peptide sequences of the invention are described below.

Thus, as it is mentioned above the invention relates to variants of amino acid sequences set forth in SEQ ID NOs: 1-29.

In one aspect the term "variant of a peptide sequence" means that the peptides may be modified, for example by substitution of one or more of the amino acid residues. Both L-amino acids and D-amino acids may be used. Other modification may comprise derivatives such as esters, sugars, etc. Examples are methyl and acetyl esters.

In another aspect "variants" may be understood as exhibiting amino acid sequences gradually differing from the preferred predetermined sequence, as the number and scope of insertions, deletions and substitutions including conservative substitutions increase. This difference is measured as a reduction in homology between the predetermined sequence and the variant.

In still another aspect, variants of the peptide fragments according to the invention may comprise, within the same variant, or fragments thereof or among different variants, or fragments thereof, at least one substitution, such as a plurality of substitutions introduced independently of one another. Variants of the complex, or fragments thereof may thus comprise conservative substitutions independently of one another, wherein at least one glycine (Gly) of said variant, or fragments thereof is substituted with an amino acid selected from the group of amino acids consisting of Ala, Val, Leu, and Ile, and independently thereof, variants, or fragments thereof, wherein at least one alanine (Ala) of said variants, or fragments thereof is substituted with an amino acid selected from the group of amino acids consisting of Gly, Val, Leu, and Ile, and independently thereof, variants, or fragments thereof, wherein at least one valine (Val) of said variant, or fragments thereof is substituted with an amino acid selected from the group of amino acids consisting of Gly, Ala, Leu, and Ile, and independently thereof, variants, or fragments thereof, wherein at least one leucine (Leu) of said variant, or fragments thereof is substituted with an amino acid selected from the group of amino acids consisting of Gly, Ala, Val, and Ile, and independently thereof, variants, or fragments thereof, wherein at least one isoleucine (Ile) of said variants, or fragments thereof is substituted with an amino acid selected from the group of amino acids consisting of Gly, Ala, Val and Leu, and independently thereof, variants, or fragments thereof wherein at least one aspartic acids (Asp) of said variant, or fragments thereof is substituted with an amino acid selected from the group of amino acids consisting of Glu, Asn, and Gln, and independently thereof, variants, or fragments thereof, wherein at least one aspargine (Asn) of said variants, or fragments thereof is substituted with an amino acid selected from the group of amino acids consisting of Asp, Glu, and Gln, and independently thereof, variants, or fragments thereof, wherein at least one glutamine (Gln) of said variants, or fragments thereof is substituted with an amino acid selected from the group of amino acids consisting of Asp, Glu, and Asn, and wherein at least one phenylalanine (Phe) of said variants, or fragments thereof is substituted with an amino acid selected from the group of amino acids consisting of Tyr, Trp, His, Pro, and preferably selected from the group of amino acids consisting of Tyr and Trp, and independently thereof, variants, or fragments thereof, wherein at least one tyrosine (Tyr) of said variants, or fragments thereof is substituted with an amino acid selected from the group of amino acids consisting of Phe, Trp, His, Pro, preferably an amino acid selected from the group of amino acids consisting of Phe and Trp, and independently thereof, variants, or fragments thereof, wherein at least one arginine (Arg) of said fragment is substituted with an amino acid selected from the group of amino acids consisting of Lys and His, and independently thereof, variants, or fragments thereof, wherein at least one lysine (Lys) of said variants, or fragments thereof is substituted with an amino acid selected from the group of amino acids consisting of Arg and His, and independently thereof, variants, or fragments thereof, and independently thereof, variants, or fragments thereof, and wherein at least one proline (Pro) of said variants, or fragments thereof is substituted with an amino acid selected from the group of amino acids consisting of Phe, Tyr, Trp, and His, and independently thereof, variants, or fragments thereof, wherein at least one cysteine (Cys) of said variants, or fragments thereof is substituted with an amino acid selected from the group of amino acids consisting of Asp, Glu, Lys, Arg, His, Asn, Gln, Ser, Thr, and Tyr.

It thus follows from the above that the same functional equivalent of a peptide fragment, or fragment of said functional equivalent may comprise more than one conservative amino acid substitution from more than one group of conservative amino acids as defined herein above. The term "conservative amino acid substitution" is used synonymously herein with the term "homologous amino acid substitution".

The groups of conservative amino acids are as the following:

P, A, G (neutral, weakly hydrophobic),

S, T (neutral, hydrophilic)

Q, N (hydrophilic, acid amine)

E, D (hydrophilic, acidic)

H, K, R (hydrophilic, basic)

L, I, V, M, F, Y, W (hydrophobic, aromatic)

C (cross-link forming)

According to the invention, a variant may be an amino acid sequence having at least 60%, more preferably at least 70%, more preferably at least 80%, more preferably at least 90%, more preferably 95%, even more preferably 97%, 98% or 99% homology to an amino acid sequence selected from SEQ ID NOs:1-29, or it may be an amino acid sequence having at least 60%, more preferably at least 70%, more preferably at least 80%, more preferably at least 90%, more preferably 95%, even more preferably 97%, 98% or 99% positive amino acid matches compared to an amino acid sequence selected from SEQ ID NOs:1-29. A positive amino acid match is defined herein as an identity or similarity defined by physical and/or chemical properties of the amino acids having the same position in two compared sequences. Preferred positive amino acid matches of the present invention are K to R, E to D, L to M, Q to E, I to V, I to L, A to S, Y to W, K to Q, S to T, N to S and Q to R. The homology of one amino acid sequence with another amino acid is defined as a percentage of identical amino acids in the two collated sequences. The wording "sequence homology" is used herein synonymously with the term "sequence similarity". The sequence homology, as already mentioned above, may be routinely calculated using well known algorithms such as BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, or BLOSUM 90;

Substitution of amino acids in a peptide sequence of the invention which results in formation of the peptide sequence variants included in the scope of the invention may in one embodiment be made based upon their hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In some embodiments the following variants may be preferred:
1. a variant which is an amino acid sequence of at least 6 amino acid residues having at least 65% sequence similarity with a sequence selected from the sequences of SEQ ID NOs:1-29, preferably an amino acid sequence of 6 to 18 contiguous amino acid residues, which has more then 70% sequence similarity with a sequence selected from the sequences of SEQ ID NOs:1-29, such as from 71% to 80% similarity, preferably from 81% to 85%, more preferably from 86% to 90%, even more preferably from 91% to 95%, and even more preferably more then 95% of sequence similarity, such as 96-99% similarity.
2. a variant which consists of a sequence of SEQ ID NOs:1-29, wherein said sequence comprising one or more amino acid residues which is/are covalently attached to a derivative of a sugar or lipid, or another derivative such as for example a phosphoryl or acetyl residue, or may comprise any other chemical moieties which do not affect biological activity of the sequence.

When referred to a fragment of an amino acid sequence selected from SEQ ID NOs:1-29, such fragment according to the invention has the length of at least 40% of the length of the selected sequence, more preferably at least 50%, more preferably at least 60%, more preferably at least 70%, more preferably at least 80%, more preferably at least 90%, more preferably at least 95% of the length. In preferred embodiments the invention concerns fragments having the amino acid sequences identified as SEQ ID NOs:30-39.

It is understood that a fragment, variant and homologue of a selected sequence such as described above fragments and variants remain at least some biological activity of the original sequence.

According to the present invention the isolated peptide may be formulated as a part of a compound. The compound may contain a single copy of the peptide, or it may contain two or more copies of the peptide. This means that compound of the invention may be formulated as a monomer of the peptide sequence, such as containing a single individual peptide sequence, or it may be formulated as a multimer containing two or more peptide sequences. Said multimers may comprise two or more copies of the same amino acid sequence or they may comprise two or more different peptide sequences. A multimer may also comprises a combination of a selected amino sequence and one or more fragments thereof.

In one embodiment the compound may contain two identical or different amino acid sequences, such compound is defined herein as dimer, in another embodiment the compound may contain more then two identical or different amino acid sequences, such for example three, four or more amino acid sequences. The present invention preferably relates to compounds containing two or four peptide sequences of the Amino acid sequences of the compound may be connected to each other via a peptide bond, or kinked via a linker molecule or grouping.

In a preferred embodiment, the compound contains two or four identical copies of a peptide sequence comprising or consisting of an amino acid sequence selected from SEQ ID NOs:1-39, wherein said peptide sequences are connected to each other via a linker molecule or grouping. One example of such linking grouping may be an achiral di-, tri- or tetracarboxylic acid. Suitable achiral di-, tri- or tetracarboxylic acids and a method of production such a compound (a ligand presentation assembly method (LPA)) are discussed in detail in WO 00/18791. Another example of a possible linker may be a residue of lysine. Individual peptide sequences may be attached to the core consisting of tree lysine residues. Such compounds are called dendritic multimer (dendrimer) or the MAP type compounds and well known in the art (PCT/US90/02039, Lu et al., (1991) Mol. Immunol. 28:623-630; Defoort et al., (1992) Int J Pept Prot Res. 40:214-221; Drijfhout et al. (1991) Int J Pept Prot Res. 37:27-32). The MAPs are at present widely used in research and in medical applications. It is a preferred embodiment of the invention to provide a dendrimeric compound comprising four individual peptides comprising or consisting of an amino acid sequence selected from SEQ ID NOs:1-39.

Although multimeric presentation such as the LPA or MAP is preferred, other known types of multimeric compounds comprising two or more individual sequences of the invention are also included in the scope of the invention and may be prepared according to the described in the are techniques when needed.

2. Biological Activity

A peptide sequence of the invention and a compound comprising the sequence possess biological activity. The invention preferably relates to a biological activity associated with the activity of the ErbB receptor.

According to the invention the peptide and compound comprising thereof are capable of binding to the ErbB receptor. The ErbB receptor may be ErbB1, ErbB2, ErbB3 or ErbB3 receptor in different preferred embodiments.

The peptide according to the invention is capable of binding to the ErbB receptor with the binding affinity (Kd) of between $10^{-6}$ M and $10^{-9}$ M.

Binding of the peptide to the receptor according to the invention leads to modulating activity of ErbB. The term "modulating" includes both stimulating and inhibiting. Accordingly, the peptide of the invention may be capable of either activating or inhibiting depending on particularity of the amino acid sequence of the peptide and also on the receptor environment, e.g. whether the ErbB receptor other ligands are present in the receptor environment. As described above, the peptide may comprise different peptide fragments of the ErbB receptor. Some of these fragments have a capacity to bind to ErbB and inhibit the receptor, in contrary, the other are capable of stimulating activity of ErbB via binding to the receptor. One non-limited example of such peptide may be a peptide comprising or consisting of SEQ ID NO:3 or SEQ ID NO:6 of the present invention. These peptides are capable of either activating or inhibiting ErbB depending on the presence or absence of an ErbB ligand, e.g. EGF.

The ErbB receptor is a major receptor involved in regulation of cell proliferation, differentiation, survival and motility. A compound which is capable of modulating activity of ErbB is thus also capable of modulating physiological responses dependent on ErbB activity. Thus, any physiological response associated with activity of ErbB is within the scope of the invention as the peptide described herein is capable of modulating activity of the receptor. Preferred biological activities of the peptide include modulating cell proliferation, cell differentiation, cell survival and/or cell motility.

In some embodiments the capability of the peptide to inhibit cell proliferation, cell differentiation, cell survival and/or cell motility may be preferred, for example when cancer cells are concerned. In another preferred embodiments the capability of stimulating cell proliferation, cell differentiation, cell survival and/or cell motility may be preferred, for example when stem cells are concerned, e.g. neural or glial progenitor cells.

Non-limited examples of biological activity of peptides of the invention and compounds comprising thereof are described below, one example of these is the effect of the peptides of the invention on cell motility.

Cell migration is required during development of the nervous system, wound healing and tumor invasion. The correct formation and normal function of the nervous system both require that the majority of neurons migrate throughout the developing nervous system from their sites of origin to their final positions.

Some types of cells maintain a capacity to move also in a mature organism, whereas the other types lose it. In some extreme conditions such as in disease or trauma, a capability of a cell to move may define the onset of rescue or death from the disease, such as wound healing or cancer cells invasion and metastases. Therefore, substances with the potential to modulate cell motility, such as certain endogenous trophic factors, are prime targets in the search for compounds that for example facilitate the recovery from trauma, prevent the dissemination of cancer cells or inhibit the spreading of inflammation. To evaluate the potential of the described above peptide compounds, the ability of modulating of signalling related to cell motility, interfering with cell adhesion, stimulating or inhibiting cell motility, may be investigated. Compounds of the present invention are capable of modulating cell motility, i.e. inhibiting and/or stimulating, and they are, therefore, considered to be good candidate compounds for inhibiting for example invasion and dissemination of cancer cells as well as inhibiting of any type cell invasion in conditions when such inhibition is required.

According to the present invention a peptide comprising at least one of the above described sequences is capable of modulating cell motility, i.e. inhibiting or stimulating. The invention concerns the level of modulating, which is estimated to be of about 25% to about 50% or more. The term "motility" is defined herein as displacement of a cell from a place where it was to another place in a certain period of time, and in the present application cell motility is estimated as the Euclidean distance between two points corresponding to the initial and final positions of the cell. When considering quantification of cell motility and the inhibitory potential of compounds, such as the above mentioned "value" of inhibition or motility, the present application relates to the "values" defined such parameters as the rate of diffusion (R), mean-cell speed (Sτ) and locomotive index (LI) of cells. The later parameters are commonly used in the art for quantification of cell motility and described for example by Walmod et al. (2001) Methods Mol Biol. 161:59-83, and featured below.

Analysis of cell motility may be done by using any available methods and assays developed in the art for the purpose. It may be performed as for example described in Examples of the present application.

3. Production of Peptide Sequences

Peptides of the present invention are preferably produced synthetically. However, recombinant production of the compounds may also be used Recombinant Production Thus, in one embodiment the peptide sequences of the invention may be produced by use of recombinant DNA technologies.

The DNA sequence encoding a peptide or the corresponding full-length protein the peptide originates from may be prepared synthetically by established standard methods, e.g. the phosphoamidine method described by Beaucage and Caruthers, 1981, Tetrahedron Lett. 22:1859-1869, or the method described by Matthes et al., 1984, EMBO J. 3:801-805. According to the phosphoamidine method, oligonucleotides are synthesised, e.g. in an automatic DNA synthesiser, purified, annealed, ligated and cloned in suitable vectors.

The DNA sequence encoding a peptide may also be prepared by fragmentation of the DNA sequences encoding the corresponding full-length protein of peptide origin, using DNAase I according to a standard protocol (Sambrook et al., Molecular cloning: A Laboratory manual. 2 rd ed., CSHL Press, Cold Spring Harbor, N.Y., 1989). The present invention relates to full-length proteins selected from the groups of proteins identified above. The DNA encoding the full-length proteins of the invention may alternatively be fragmented using specific restriction endonucleases. The fragments of DNA are further purified using standard procedures described in Sambrook et al., Molecular cloning: A Laboratory manual. 2 rd ed., CSHL Press, Cold Spring Harbor, N.Y., 1989.

The DNA sequence encoding a full-length protein may also be of genomic or cDNA origin, for instance obtained by preparing a genomic or cDNA library and screening for DNA sequences coding for all or part of the full-length protein by hybridisation using synthetic oligonucleotide probes in accordance with standard techniques (cf. Sambrook et al., Molecular Cloning: A Laboratory Manual, 2nd Ed., Cold Spring Harbor, 1989). The DNA sequence may also be prepared by polymerase chain reaction using specific primers, for instance as described in U.S. Pat. No. 4,683,202 or Saiki et al., 1988, Science 239:487-491.

The DNA sequence is then inserted into a recombinant expression vector, which may be any vector, which may conveniently be subjected to recombinant DNA procedures. The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding a peptide or a full-length protein should be operably connected to a suitable promoter sequence. The promoter may be any DNA sequence, which shows transcriptional activity in the host cell of choice and may be derived from genes encoding proteins either homologous or heterologous to the host cell. Examples of suitable promoters for directing the transcription of the coding DNA sequence in mammalian cells are the SV 40 promoter (Subramani et al., 1981, Mol. Cell Biol. 1:854-864), the MT-1 (metallothionein gene) promoter (Palmiter et al., 1983, Science 222: 809-814) or the adenovirus 2 major late promoter. A suitable promoter for use in insect cells is the polyhedrin promoter (Vasuvedan et al., 1992, FEBS Lett. 311:7-11). Suitable promoters for use in yeast host cells include promoters from yeast glycolytic genes (Hitzeman et al., 1980, J. Biol. Chem. 255:12073-12080; Alber and Kawasaki, 1982, J. Mol. Appl. Gen. 1: 419-434) or alcohol dehydrogenase genes (Young et al., 1982, in Genetic Engineering of Microorganisms for Chemicals, Hollaender et al, eds., Plenum Press, New York), or the TPI1 (U.S. Pat. No. 4,599,311) or ADH2-4-c (Russell et al., 1983, Nature 304: 652-654) promoters. Suitable promoters for use in filamentous fungus host cells are, for instance, the ADH3 promoter (McKnight et al., 1985, EMBO J. 4:2093-2099) or the tpiA promoter.

The coding DNA sequence may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An example of such a sequence (when the host cell is a mammalian cell) is the SV 40 origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hydromycin or methotrexate.

The procedures used to ligate the DNA sequences coding the peptides or full-length proteins, the promoter and the terminator, respectively, and to insert them into suitable vectors containing the information necessary for replication, are well known to persons skilled in the art (cf., for instance, Sambrook et al., op.cit.).

To obtain recombinant peptides of the invention the coding DNA sequences may be usefully fused with a second peptide coding sequence and a protease cleavage site coding sequence, giving a DNA construct encoding the fusion protein, wherein the protease cleavage site coding sequence positioned between the HBP fragment and second peptide coding DNA, inserted into a recombinant expression vector, and expressed in recombinant host cells. In one embodiment, said second peptide selected from, but not limited by the group comprising glutathion-S-reductase, calf thymosin, bacterial thioredoxin or human ubiquitin natural or synthetic variants, or peptides thereof. In another embodiment, a peptide sequence comprising a protease cleavage site may be the Factor Xa, with the amino acid sequence IEGR, enterokinase, with the amino acid sequence DDDDK, thrombin, with the amino acid sequence LVPR/GS, or *Acharombacter lyticus*, with the amino acid sequence XKX, cleavage site.

The host cell into which the expression vector is introduced may be any cell which is capable of expression of the peptides or full-length proteins, and is preferably a eukaryotic cell, such as invertebrate (insect) cells or vertebrate cells, e.g. *Xenopus laevis* oocytes or mammalian cells, in particular insect and mammalian cells. Examples of suitable mammalian cell lines are the HEK293 (ATCC CRL-1573), COS (ATCC CRL-1650), BHK (ATCC CRL-1632, ATCC CCL-10) or CHO (ATCC CCL-61) cell lines. Methods of transfecting mammalian cells and expressing DNA sequences introduced in the cells are described in e.g. Kaufman and Sharp, J. Mol. Biol. 159, 1982, pp. 601-621; Southern and Berg, 1982, J. Mol. Appl. Genet. 1:327-341; Loyter et al., 1982, Proc. Natl. Acad. Sci. USA 79: 422-426; Wigler et al., 1978, Cell 14:725; Corsaro and Pearson, 1981, in Somatic Cell Genetics 7, p. 603; Graham and van der Eb, 1973, Virol. 52:456; and Neumann et al., 1982, EMBO J. 1:841-845.

Alternatively, fungal cells (including yeast cells) may be used as host cells. Examples of suitable yeast cells include cells of *Saccharomyces* spp. or *Schizosaccharomyces* spp., in particular strains of *Saccharomyces cerevisiae*. Examples of other fungal cells are cells of filamentous fungi, e.g. *Aspergillus* spp. or *Neurospora* spp., in particular strains of *Aspergillus oryzae* or *Aspergillus niger*. The use of *Aspergillus* spp. for the expression of proteins is described in, e.g., EP 238 023.

The medium used to culture the cells may be any conventional medium suitable for growing mammalian cells, such as a serum-containing or serum-free medium containing appropriate supplements, or a suitable medium for growing insect, yeast or fungal cells. Suitable media are available from commercial suppliers or may be prepared according to published recipes (e.g. in catalogues of the American Type Culture Collection).

The peptides or full-length proteins recombinantly produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e.g. HPLC, ion exchange chromatography, affinity chromatography, or the like.

Synthetic Production of Individual Peptide Sequences

The methods for synthetic production of peptides are well known in the art. Detailed descriptions as well as practical advice for producing synthetic peptides may be found in Synthetic Peptides: A User's Guide (Advances in Molecular Biology), Grant G. A. ed., Oxford University Press, 2002, or in: Pharmaceutical Formulation: Development of Peptides and Proteins, Frokjaer and Hovgaard eds., Taylor and Francis, 1999.

Peptides may for example be synthesised by using Fmoc chemistry and with Acm-protected cysteines. After purification by reversed phase HPLC, peptides may be further processed to obtain for example cyclic or C- or N-terminal modified isoforms. The methods for cyclization and terminal modification are well-known in the art and described in detail in the above-cited manuals.

In a preferred embodiment the individual peptide sequences of the invention are produced synthetically, in particular, by the Sequence Assisted Peptide Synthesis (SAPS) method described in the above mentioned manuals.

By SAPS peptides may be synthesised either batchwise in a polyethylene vessel equipped with a polypropylene filter for filtration or in the continuous-flow version of the polyamide solid-phase method (Dryland, A. and Sheppard, R. C., (1986) J. Chem. Soc. Perkin Trans. I, 125-137) on a fully automated peptide synthesiser using 9-fluorenylmethyloxycarbonyl (Fmoc) or tert.-Butyloxycarbonyl, (Boc) as N-a-amino protecting group and suitable common protection groups for side-chain functionality.

Otherwise, the synthesis of an individual peptide sequence of the invention may be ordered and purchased from a commercial manufacturer.

Individual peptide sequences may further be formulated as multimers described above using well-known in the art techniques, for examples dimers of the peptide sequences may be obtained by the LPA method described in detail in WO 00/18791, dendrimeric peptides may be obtained by a procedure described in PCT/US90/02039.

4. Antibody

Another aspect of the present invention relates to an antibody, antigen binding fragment or recombinant protein thereof capable of recognizing and selectively binding to an epitope comprising or comprised by an amino acid sequence selected from SEQ ID NOs:1-39, or fragment, variant or homologue of said sequence. In a preferred embodiment the epitope comprising an amino acid sequence of the invention is located in the dimerisation loop, autoinhibitory loop or membrane proximal domain of the ErbB receptor. In one embodiment the antibody is an antibody that recognizes and binds to an epitope comprising a sequence selected from SEQ ID NOs:1-6 or 30-39 or a fragment, or variant or homologue of said sequences, in another embodiment the antibody recognizes an epitope comprising a sequence selected from SEQ ID NOs:7-18, or a fragment, or variant or homologue of said sequences. In still another preferred embodiment the antibody recognizes and binds to an epitope comprising a sequence selected from SEQ ID NOs:19-29, or a fragment, or variant or homologue of said sequences.

By the term "epitope" is meant the specific group of atoms (on an antigen molecule) that is recognized by (that antigen's) antibodies (thereby causing an immune response). The term "epitope" is the equivalent to the term "antigenic determinant". The epitope may comprise 3 or more amino acid residues, such as for example 4, 5, 6, 7, 8 amino acid residues, located in close proximity, such as within a contiguous amino acid sequence, or located in distant parts of the amino acid sequence of an antigen, but due to protein folding have been approached to each other.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Novotny J, & Haber E. Proc Natl Acad Sci USA. 82(14):4592-6, 1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino acid sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely a adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

The term "antibody fragment" is used herein interchangeably with the term "antigen binding fragment".

Antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it is has similar or immunological properties relative to antibody that binds with specificity to an epitope comprising a peptide sequence selected from any of the sequences identified herein as SEQ ID NOs: 1-39, or a fragment of said sequences. Thus, in context of the present invention the term "antibody fragment" is identical to term "antigen binding fragment".

Antibody fragments retain some ability to selectively bind with its antigen or receptor. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule.

Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction.

(4) F(ab')$_2$ is a dimer of two Fab' fragments held together by two disulfide bonds.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the VH and VL domains that enables the sFv to form the desired structure for antigen binding. For a review of sFv see Pluckthun in The Pharmacology of Monoclonal Antibodies 113: 269-315 Rosenburg and Moore eds. Springer-Verlag, NY, 1994.

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad. Sci. USA 90: 6444-6448 (1993).

The invention contemplate both polyclonal and monoclonal antibody, antigen binding fragments and recombinant proteins thereof which are capable of binding an epitope according to the invention.

The preparation of polyclonal antibodies is well-known to those skilled in the art. See, for example, Green et al. 1992. Production of Polyclonal Antisera, in: Immunochemical Protocols (Manson, ed.), pages 1-5 (Humana Press); Coligan, et al., Production of Polyclonal Antisera in Rabbits, Rats Mice and Hamsters, in: Current Protocols in Immunology, section 2.4.1, which are hereby incorporated by reference.

The preparation of monoclonal antibodies likewise is conventional. See, for example, Kohler & Milstein, Nature, 256: 495-7 (1975); Coligan, et al., sections 2.5.1-2.6.7; and Harlow, et al., in: Antibodies: A Laboratory Manual, page 726, Cold Spring Harbor Pub. (1988), Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG). In: Methods in Molecular Biology, 1992, 10:79-104, Humana Press, NY.

Methods of in vitro and in vivo manipulation of monoclonal antibodies are well known to those skilled in the art. For example, the monoclonal antibodies to be used in accordance with the present invention may be made by the hybridoma method first described by Kohler and Milstein, 1975, Nature 256, 495-7, or may be made by recombinant methods, e.g., as described in U.S. Pat. No. 4,816,567. The monoclonal antibodies for use with the present invention may also be isolated from phage antibody libraries using the techniques described in Clackson et al., 1991, Nature 352: 624-628, as well as in Marks et al., 1991, J Mol Biol 222: 581-597. Another method involves humanizing a monoclonal antibody by recombinant means to generate antibodies containing human specific and recognizable sequences. See, for review, Holmes, et al., 1997, J Immunol 158:2192-2201 and Vaswani, et al., 1998, Annals Allergy, Asthma & Immunol 81:105-115.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al., 1984, Proc Natl Acad Sci 81: 6851-6855.

Methods of making antibody fragments are also known in the art (see for example, Harlow and Lane, Antibodies: A Laboratory Manual, Cold Spring Harbor Laboratory, NY, 1988, incorporated herein by reference). Antibody fragments of the present invention can be prepared by proteolytic hydrolysis of the antibody or by expression in $E.\ coli$ of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. No. 4,036,945 and U.S. Pat. No. 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as $E.\ coli$. The recombinant host cells synthesize a single polypeptide chain with a linker peptide bridging the two V domains. Methods for producing sFvs are described, for example, by Whitlow, et al., 1991, In: Methods: A Companion to Methods in Enzymology, 2:97; Bird et al., 1988, Science 242:423-426; U.S. Pat. No. 4,946,778; and Pack, et al., 1993, BioTechnology 11:1271-77.

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., Methods: a Companion to Methods in Enzymology, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', $F(ab')_2$ or other antigen-binding subsequences of antibodies) that contain a minimal sequence derived from non-human immunoglobulin, such as the epitope recognising sequence. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity. Humanized antibody(es) containing a minimal sequence(s) of antibody(es) of the invention, such as a sequence(s) recognising an epitope(s) described herein, is one of the preferred embodiments of the invention.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., 1986, Nature 321, 522-525; Reichmann et al., 1988, Nature 332, 323-329; Presta, 1992, Curr Op Struct Biol 2:593-596; Holmes et al., 1997, J Immunol 158:2192-2201 and Vaswani, et al., 1998, Annals Allergy, Asthma & Immunol 81:105-115.

The generation of antibodies may be achieved by any standard methods in the art for producing polyclonal and monoclonal antibodies using natural or recombinant fragments of ErbB which comprise an amino acid sequence selected from SEQ ID NOs:1-39, as an antigen. Such antibodies may be also generated using variants, homologues or fragments of peptide sequences of SEQ ID NOs:1-39, or any other immunogenic peptide sequences or immunogenic fragments thereof, which meet the following criteria:

(i) being a contiguous amino acid sequence of at least 6 amino acids, and
(ii) comprising at least 3 contiguous amino acid residues of any of the sequences SEQ ID NOs:1-39.

The antibodies may also be produced in vivo by the individual to be treated, for example, by administering an immunogenic fragment according to the invention to said individual. Accordingly, the present invention further relates to a vaccine comprising an immunogenic fragment described above.

The application also relates to a method for producing an antibody of the invention said method comprising a step of providing of an immunogenic fragment described above.

The invention relates both to 1) an antibody, which is capable of modulating, such as enhancing or attenuating, biological function of the ErbB receptor in particular a function related to cell proliferation, differentiation and/or cell motility, 2) an antibody, which can recognise and specifically bind to the ErbB receptor without modulating biological activity thereof.

The invention relates to use of the described above antibodies for 1) therapeutic applications involving the modulation of activity of the ErbB receptors and/or ErbB ligands; 2) modulating cellular and physiological processes including cell differentiation, proliferation and/or motility, 3) detecting and/or monitoring the ErbB receptors in vitro and/or in vivo for diagnostic purposes and 4) research purposes.

In one embodiment the invention relates to a pharmaceutical composition comprising an antibody described above.

5. Medicament

The present invention provides peptide sequences and compounds, capable i) modulating cell proliferation; ii) modulating cell differentiation; iii) modulating cell motility; iv) modulating activity of the ErbB receptor or ErbB ligands. Accordingly, the compounds may be useful for treatment of diseases and/or conditions, wherein said modulating is required.

The ErbB receptor and its ligand family has been shown to be implicated in a number of pathologic conditions and diseases.

EGFR or ErbB1 has been causally implicated in human malignancy and, in particular, increased expression of this gene has been observed in more aggressive carcinomas of the breast, bladder, lung and stomach. Increased EGFR expression has been reported to be often associated with increased production of the EGFR ligand, transforming growth factor-alpha (TGF-alpha), by the same tumor cells, resulting in receptor activation by an autocrine stimulatory pathway. (Baselga et al., Pharmac. Ther. 64:127-154 (1994)). Monoclonal antibodies directed against the EGFR, or its ligands TGF-alpha and EGF, have been evaluated as therapeutic agents in the treatment of such malignancies. (See, e.g., Baselga et al., supra; Masui et al., Cancer Research 44: 1002-1007 (1984); Wu et al., J. Clin. Invest. 95:1897-1905 (1995)).

The a member of the ErbB subfamily, p185<neu>, was originally identified as the product of the transforming gene from neuroblastomas of chemically treated rats. The neu gene (also called erbB2 and HER2) encodes a 185 kDa receptor protein tyrosine kinase. Amplification and/or overexpression of the human ErbB2 gene correlates with a poor prognosis in breast and ovarian cancers. (Slamon et al., Science 235:177-182 (1987); and Slamon et al., Science 244:707-712 (1989); U.S. Pat. No. 4,968,603). Overexpression of ErbB2 has been observed with other carcinomas including carcinomas of the stomach, endometrium, salivary gland, lung, kidney, colon and bladder. Accordingly, Slamon et al. in U.S. Pat. No. 4,968,603 describe and claim various diagnostic assays for determining ErbB2 gene amplification or expression in tumor cells.

Antibodies directed against the rat p185<neu> and human ErbB2 gene products have been described. For instance, Drebin et al., Cell 41:695-706 (1985); Meyers et al., Methods Enzym. 198:277-290 (1991); and WO 94/22478 describe antibodies directed against the rat gene product, p185<neu>. Hudziak et al., Mol. Cell. Biol. 9:1165-1172 (1989) describe the generation of a panel of anti-ErbB2 antibodies which were characterized using the human breast tumor cell line SKBR3. Other anti-ErbB2 antibodies have also been reported in the literature. (See, e.g., U.S. Pat. Nos. 5,821,337 and 5,783,186; WO 94/00136; Tagliabue et al., Int. J. Cancer 47:933-937 (1991); McKenzie et al., Oncogene 4:543-548 (1989); Maier et al., Cancer Res. 51:5361-5369 (1991); Bacus et al., Molecular Carcinogenesis 3:350-362 (1990); Xu et al., Int. J. Cancer 53:401408 (1993); Kasprzyk et al., Cancer Research 52:2771-2776 (1992); Hancock et al., Cancer Research 51:45754580 (1991); Shawver et al., Cancer Research 54:1367-1373 (1994); Arteaga et al., Cancer Research 54:3758-3765 (1994); Harwerth et al., J. Biol. Chem. 267:15160-15167 (1992)).

A further related gene, called erbB3 or HER3, has also been described. See U.S. Pat. Nos. 5,183,884 and 5,480,968; Kraus et al., Proc. Natl. Acad. Sci. USA 86:9193-9197

(1989); EP patent application number 444,961A1; and Kraus et al., Proc. Natl. Acad. Sci. USA 90:2900-2904 (1993). Kraus et al. (1989) discovered that markedly elevated levels of erbB3 mRNA were present in certain human mammary tumor cell lines indicating that erbB3, like erbB1 and erbB2, may play a role in human malignancies. Also, Kraus et al., supra (1993) showed that EGF-dependent activation of the ErbB3 catalytic domain of a chimeric EGFR/ErbB3 receptor resulted in a proliferative response in transfected NIH-3T3 cells. This is now believed to be the result of endogenous ErbB1 or ErbB2 in NIH-3T3. Furthermore, these researchers demonstrated that some human mammary tumor cell lines display a significant elevation of steady-state ErbB3 tyrosine phosphorylation further indicating that this receptor may play a role in human malignancies. The role of erbB3 in cancer has been explored by others. It has been found to be overexpressed in breast (Lemoine et al., Br. J. Cancer 66:1116-1121 (1992)), gastrointestinal (Poller et al., J. Pathol. 168:275-280 (1992), Rajkumer et al., J. Pathol. 170:271-278 (1993), and Sanidas et al., Int. J. Cancer 54:935-940 (1993)), and pancreatic cancers (Lemoine et al., J. Pathol. 168:269-273 (1992); Friess et al., Clinical Cancer Research 1: 1413-1420 (1995)).

The class I subfamily of epidermal growth factor receptor protein tyrosine kinases has been further extended to include the ErbB4 receptor. (See EP patent application number 599, 274; Plowman et al., Proc. Natl. Acad. Sci. USA 90:1746-1750 (1993); and Plowman et al., Nature 366:473-475 (1993)). Plowman et al. found that increased ErbB4 expression closely correlated with certain carcinomas of epithelial origin, including breast adenocarcinomas. Diagnostic methods for detection of human neoplastic conditions (especially breast cancers) which evaluate ErbB4 expression are described in EP Appln. No. 599,274.

Various ligands which bind and/or activate such ErbB receptors have been described in the literature. The ligands include the polypeptides referred to as EGF (Savage et al., J. Biol. Chem. 247:7612-7621 (1972)), TGF-alpha (Marquardt et al., Science 223:1079-1082 (1984)), amphiregulin (Shoyab et al., Science 243:1074-1076 (1989); Kimura et al., Nature 348:257-260 (1990); Cook et al., Mol. Cell. Biol. 11:2547-2557 (1991)), heparin-binding EGF (HB-EGF)(Higashiyama et al., Science 251:936-939 (1991)), betacellulin (Shing et al., Science 259:1604-1607 (1993)), and epiregulin (Toyoda et al., J. Biol. Chem. 270:7495-7500 (1995)). ErbB1 is bound by six different ligands; epidermal growth factor (EGF), TGF-alpha, amphiregulin, HB-EGF, betacellulin, and epiregulin. (See also, e.g., Groenen et al., Growth Factors 11:235-257 (1994)).

A family of heregulin proteins resulting from alternative splicing of a single gene are ligands for ErbB3 and ErbB4. As discussed further below, the heregulin family includes NDFs, GGFs, and ARIA. (Groenen et al., Growth Factors 11:235-257 (1994); Lemke, Molec. & Cell. Neurosc. 7:247-262 (1996); Lee et al., Pharm. Rev. 47:51-85 (1995)). Further ErbB ligands have been identified-neuregulin-2 (NRG-2) which is reported to bind either ErbB3 or ErbB4 (Chang et al., Nature 387:509-512 (1997); Carraway et al., Nature 387:512-516 (1997)) and neuregulin-3 which binds ErbB4 (Zhang et al., Proc. Natl. Acad. Sci. 94:9562-9567 (1997)). HB-EGF, betacellulin, and epiregulin also bind to ErbB4.

While EGF and TGF-alpha do not bind ErbB2, EGF stimulates ErbB1 and ErbB2 to form a heterodimer, which activates ErbB1 and results in transphosphorylation of ErbB2 in the heterodimer. Dimerization and/or transphosphorylation appears to activate the ErbB2 tyrosine kinase. Likewise, when ErbB3 is co-expressed with ErbB2, an active signaling complex is formed and antibodies directed against ErbB2 are capable of disrupting the complex. (Sliwkowski et al., J. Biol. Chem. 269:14661-14665 (1994)). Additionally, the affinity of ErbB3 for heregulin is increased to a higher affinity state when co-expressed with ErbB2. (Levi et al., J. Neuroscience 15:1329-1340 (1995); Morrisey et al., Proc. Natl. Acad. Sci. 92:1431-1435 (1995) and Lewis et al., Cancer Research 56:1457-1465 (1996) with respect to the ErbB2-ErbB3 protein complex). ErbB4, like ErbB3, forms an active signaling complex with ErbB2. (Carraway et al., Cell 78:5-8 (1994)).

Holmes et al. isolated and cloned a family of polypeptide activators for the ErbB2 receptor which they called heregulin-alpha (HRG-alpha), heregulin-beta1 (HRG-beta1), heregulin-beta2 (HRG-beta2), heregulin-beta2-like (HRG-beta2-like), and heregulin-beta3 (HRG-beta3). (See Holmes et al., Science 256:1205-1210 (1992); WO 92/20798; and U.S. Pat. No. 5,367,060). The 45 kDa polypeptide, HRG-alpha, was purified from the conditioned medium of the MDA-MB-231 human breast cancer cell line. These researchers demonstrated the ability of the purified heregulin polypeptides to activate tyrosine phosphorylation of the ErbB2 receptor in MCF7 breast tumor cells. Furthermore, the mitogenic activity of the heregulin polypeptides on SK-BR-3 cells (which express high levels of the ErbB2 receptor) was illustrated.

While heregulins are substantially identical in the first 213 amino acid residues, they are classified into two major types, alpha and beta, based on two variant EGF-like domains which differ in their C-terminal portions. Nevertheless, these EGF-like domains are identical in the spacing of six cysteine residues contained therein. Based on an amino acid sequence comparison, Holmes et al. found that between the first and sixth cysteines in the EGF-like domain, HRGs were 45% similar to heparin-binding EGF-like growth factor (HB-EGF), 35% identical to amphiregulin (AR), 32% identical to TGF-alpha, and 27% identical to EGF.

The 44 kDa neu differentiation factor (NDF), which is the rat equivalent of human HRG, was first described by Peles et al., Cell, 69:205-216 (1992); and Wen et al., Cell, 69:559-572 (1992). Like the HRG polypeptides, NDF has an immunoglobulin (Ig) homology domain followed by an EGF-like domain and lacks a N-terminal signal peptide. Subsequently, Wen et al., Mol. Cell. Biol., 14(3): 1909-1919 (1994) carried out "exhaustive cloning" to extend the family of NDFs. This work revealed six distinct fibroblastic pro-NDFs. Adopting the nomenclature of Holmes et al., the NDFs are classified as either alpha or beta polypeptides based on the sequences of the EGF-like domains. These researchers conclude that different NDF isoforms are generated by alternative splicing and perform distinct tissue-specific functions. See also EP 505 148; WO 93/22424; and WO 94/28133 concerning NDF.

Falls et al., Cell, 72:801-815 (1993) describe another member of the heregulin family which they call acetylcholine receptor inducing activity (ARIA) polypeptide. The chicken-derived ARIA polypeptide stimulates synthesis of muscle acetylcholine receptors. See also WO 94/08007. ARIA is a type I heregulin with a beta type EGF domain.

Marchionni et al., Nature, 362:312-318 (1993) identified several bovine-derived proteins which they call glial growth factors (GGFs). These GGFs share the Ig-like domain and EGF-like domain with the other heregulin proteins described above, but also have an amino-terminal kringle domain. GGFs generally do not have the complete glycosylated spacer region between the Ig-like domain and EGF-like domain. Only one of the GGFs, GGFII, possessed a N-terminal signal peptide. See also WO 92/18627; WO 94/00140; WO 94/04560; WO 94/26298; and WO 95/32724 which refer to GGFs and uses thereof.

Ho et al., in J. Biol. Chem. 270(4):14523-14532 (1995), describe another member of the heregulin family called sensory and motor neuron-derived factor (SMDF). This protein has an EGF-like domain characteristic of all other heregulin polypeptides but a distinct N-terminal domain. The major structural difference between SMDF and the other heregulin polypeptides is that SMDF lacks the Ig-like domain and the "glyco" spacer characteristic of all the other heregulin polypeptides. Another feature of SMDF is the presence of two stretches of hydrophobic amino acids near the N-terminus.

While heregulin polypeptides were first identified based on their ability to activate the ErbB2 receptor (see Holmes et al., supra), it was discovered that certain ovarian cells expressing neu and neu-transfected fibroblasts did not bind or cross-link to NDF, nor did they respond to NDF to undergo tyrosine phosphorylation (Peles et al., EMBO J. 12:961-971 (1993)). This indicated another cellular component was necessary for conferring full heregulin responsiveness. Carraway et al. subsequently demonstrated that <125> I-rHRG [beta] 1177-244 bound to NIH-3T3 fibroblasts stably transfected with bovine erbB3 but not to non-transfected parental cells. Accordingly, the investigators suggested that ErbB3 is a receptor for HRG and mediates phosphorylation of intrinsic tyrosine residues as well as phosphorylation of ErbB2 receptor in cells which express both receptors. Carraway et al., J. Biol. Chem. 269 (19):14303-14306 (1994). Sliwkowski et al., J. Biol. Chem. 269(20):14661-14665 (1994) found that cells transfected with ErbB3 alone show low affinities for heregulin, whereas cells transfected with both ErbB2 and ErbB3 show higher affinities.

This observation correlates with the "receptor cross-talking" described previously by Kokai et al., Cell 58:287-292 (1989); Stern et al., EMBO J. 7:995-1001 (1988); and King et al., 4:13-18 (1989). These researchers found that binding of EGF to the ErbB1 resulted in activation of the ErbB1 kinase domain and cross-phosphorylation of p185. This is believed to be a result of ligand-induced receptor heterodimerization and the concomitant cross-phosphorylation of the receptors within the heterodimer. (Wada et al., Cell 61:1339-1347 (1990)).

Plowman and his colleagues have similarly studied p185<HER4>/p185<HER2> activation. They expressed p185<HER2> alone, p185<HER4> alone, or the two receptors together in human T lymphocytes and demonstrated that heregulin is capable of stimulating tyrosine phosphorylation of p185<HER4>, but could only stimulate p185<HER2> phosphorylation in cells expressing both receptors. (Plowman et al., Nature 336:473475 (1993)).

Other biological role(s) of various ErbB ligands have been investigated by several groups. For example, betacellulin has been reported to exhibit growth-promoting activity in vascular smooth muscle cells and retinal pigment epithelial cells. (Shing et al., supra). Falls et al., supra, found that ARIA plays a role in myotube differentiation, namely affecting the synthesis and concentration of neurotransmitter receptors in the postsynaptic muscle cells of motor neurons. Corfas and Fischbach demonstrated that ARIA also increases the number of sodium channels in muscle. (Corfas and Fischbach, J. Neuroscience, 13(5):2118-2125 (1993)). It has also been shown that GGFII is mitogenic for subconfluent quiescent human myoblasts and that differentiation of clonal human myoblasts in the continuous presence of GGFII results in greater numbers of myotubes after six days of differentiation. (Sklar et al., J. Cell Biochem., Abst. W462, 18D, 540 (1994)). See also WO 94/26298 published Nov. 24, 1994.

Holmes et al., supra, found that HRG exerted a mitogenic effect on mammary cell lines (such as SK-BR-3 and MCF-7). The mitogenic activity of GGFs on Schwann cells has also been reported. (See, e.g., Brockes et al., J. Biol. Chem. 255 (18):8374-8377 (1980); Lemke and Brockes, J. Neurosci. 4:75-83 (1984); Brockes et al., J. Neuroscience 4(1):75-83 (1984); Brockes et al., Ann. Neurol. 20(3):317-322 (1986); Brockes, J., Methods in Enzym. 147:217-225 (1987) and Marchionni et al., supra).

Pinkas-Kramarski et al. found that NDF seems to be expressed in neurons and glial cells in embryonic and adult rat brain and primary cultures of rat brain cells, and suggested that it may act as a survival and maturation factor for astrocytes. (Pinkas-Kramarski et al., PNAS, USA 91:9387-9391 (1994)). Meyer and Birchmeier, PNAS, USA 91:1064-1068 (1994) analyzed expression of heregulin during mouse embryogenesis and in the perinatal animal using in situ hybridization and Rnase protection experiments. See also Meyer et al., Development 124(18):3575-3586 (1997). Similarly, Danilenko et al., Abstract 3101, FASEB 8(4-5):A535 (1994) and Danilenko et al., Journal of Clinical Investigation 95(2):842-851 (1995), found that the interaction of NDF and the ErbB2 receptor is important in directing epidermal migration and differentiation during wound repair.

Ram et al., Journal of Cellular Physiology 163:589-596 (1995) evaluated the mitogenic activity of NDF on the immortalized human mammary epithelial cell line MCF-10A. Danilenko et al., J. Clin. Invest. 95:842-851 (1995) investigated whether NDF would influence epidermal migration in an in vivo model of excisional deep partial-thickness wound repair. It is reported that there were no statistically significant differences in proliferating basal and superbasal keratinocytes in control wounds vs. wounds treated with rhNDF-[alpha]2. Marikovsky et al., Oncogene 10: 1403-1411 (1995), studied the proliferative responses of an aneuploid BALB/MK continuous keratinocyte cell line and evaluated the effects of [alpha]- and [beta]-isoforms of NDF on epidermal keratinocytes.

The potential role(s) that the various ErbB ligands may play in pancreatic cell proliferation and differentiation has also been reported by several investigators. Islet cells (also referred to as Islets of Langerhans) in the pancreas are known to produce the hormones, insulin, and glucagon. Such islet cells are believed to be derived from stem cells in the fetal ductular pancreatic endothelium. (Pictet and Rutter, "Development of the embryonic pancreas", Endocrinology, Handbook of Physiology, 1972, American Physiological Society, Washington D.C., pages 25-66). In particular, during development, the pancreas forms a system of tubules composed of a single layer of undifferentiated cells, which may then differentiate into duct cells, acinar cells or islet cells. (See, e.g., LeDouarin, Cell, 53:169-171 (1998); Teitelman, Recent Prog. Hormone Res., 47:259-297 (1991)).

Various investigators have reported on the effects of particular EGF, heregulin and heregulin-related polypeptides on islet cells. In WO 95/19785 published Jul. 27, 1995, methods for treating diabetes mellitus are described wherein a combination of a gastrin/CCK receptor ligand and an EGF receptor ligand (e.g., TGF-alpha) are administered in amounts sufficient to effect differentiation of pancreatic islet precursor cells to mature insulin-secreting cells. WO 95/19785 teaches that the TGF-alpha polypeptide was not capable of stimulating differentiation of the islet precursor cells when administered alone.

WO03013485 described ErbB receptor inhibitors which are suitable for the purposes of the of inhibiting the proliferation or inducing the apoptosis of plasmocytic tumor cells.

Accordingly, all or any of the above described non-limited examples of conditions and diseases may be contemplated wherein the use of a peptide, compound and/or antibody of the invention may have a beneficial effect in treatment or prevention thereof.

Thus, a peptide, compound and/or antibody of the invention may be used for prevention, and/or treatment of
1) cancer,
2) inflammatory disease,
3) allergic condition,
4) neoangeogenesis,
5) diabetis.

The invention concerns cancer being any type of solid tumors requiring neoangiogenesis and any malignant cancer. In particular, the invention concerns cancer of the neural system.

A peptide sequence and/or compound of the invention may also be used for treating individuals having body damages due to alcohol consumption and for treating individuals suffering from prion diseases, traumatized individuals and/or individuals subjected to organ or cells transplantation.

Thus, it is an objective of the invention to use the peptide, compound, and/or antibody as a medicament and for the manufacturing a medicament. A medicament of the invention may be used for treatment any condition or disease wherein modulating activity of the ErbB receptor and/or ErbB ligand is beneficial for the treatment. Non-limited examples of such conditions and disease are described above.

The medicament of the invention may comprise an effective amount of one or more isolated peptide sequences, compounds or antibodies as described above, or it may be formulated as a pharmaceutical composition comprising an effective amount of one or more isolated peptide sequences, compounds or antibodies as described above and pharmaceutically acceptable additives. In some embodiments a medicament or pharmaceutical composition may comprise a combination of an effective amount of one or more isolated peptide sequences, compounds and/or antibodies as described above.

Thus, the invention in another aspect also concerns a pharmaceutical composition comprising at least one isolated peptide sequence, compound, and/or antibody of the invention.

A further aspect of the invention is a process of producing a pharmaceutical composition, comprising mixing an effective amount of one or more isolated peptide sequences, compounds or antibodies of the invention, or a pharmaceutical composition according to the invention with one or more pharmaceutically acceptable additives or carriers.

The invention also relates to the use a pharmaceutical composition comprising the compound of invention for treatment or prophylaxis of any of the diseases and conditions mentioned above.

In some embodiments, the inventions relates to a pharmaceutical composition comprising an antibody capable of recognizing an epitope comprising an amino acid sequence of the invention. Such pharmaceutical composition may also be useful in treatment of conditions and diseases described herein.

A medicament and/or pharmaceutical composition of the invention may suitably be formulated for oral, percutaneous, intramuscular, intravenous, intracranial, intrathecal, intracerebroventricular, intranasal or pulmonal administration.

Strategies in formulation development of medicaments and compositions based on the compounds of the present invention generally correspond to formulation strategies for any other protein-based drug product. Potential problems and the guidance required to overcome these problems are dealt with in several textbooks, e.g. "Therapeutic Peptides and Protein Formulation. Processing and Delivery Systems", Ed. A. K. Banga, Technomic Publishing AG, Basel, 1995.

Injectables are usually prepared either as liquid solutions or suspensions, solid forms suitable for solution in, or suspension in, liquid prior to injection. The preparation may also be emulsified. The active ingredient is often mixed with excipients which are pharmaceutically acceptable and compatible with the active ingredient. Suitable excipients are, for example, water, saline, dextrose, glycerol, ethanol or the like, and combinations thereof. In addition, if desired, the preparation may contain minor amounts of auxiliary substances such as wetting or emulsifying agents, pH-buffering agents, or which enhance the effectiveness or transportation of the preparation.

Formulations of the compounds of the invention can be prepared by techniques known to the person skilled in the art. The formulations may contain pharmaceutically acceptable carriers and excipients including microspheres, liposomes, microcapsules, nanoparticles or the like.

The preparation may suitably be administered by injection, optionally at the site, where the active ingredient is to exert its effect. Additional formulations which are suitable for other modes of administration include suppositories, nasal, pulmonal and, in some cases, oral formulations. For suppositories, traditional binders and carriers include polyalkylene glycols or triglycerides. Such suppositories may be formed from mixtures containing the active ingredient(s) in the range of from 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and generally contain 10-95% of the active ingredient(s), preferably 25-70%.

Other formulations are such suitable for nasal and pulmonal administration, e.g. inhalators and aerosols.

The active compound may be formulated as neutral or salt forms. Pharmaceutically acceptable salts include acid addition salts (formed with the free amino groups of the peptide compound) and which are formed with inorganic acids such as, for example, hydrochloric or phosphoric acids, or such organic acids as acetic acid, oxalic acid, tartaric acid, mandelic acid, and the like. Salts formed with the free carboxyl group may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are per kilo body weight normally of the order of several hundred µg active ingredient per administration with a preferred range of from about 0.1 µg to 5000 µg per kilo body weight. Using monomeric forms of the compounds, the suitable dosages are often in the range of from 0.1 µg to 5000 µg per kilo body weight, such as in the range of from about 0.1 µg to 3000 µg per kilo body weight, and especially in the range of from about 0.1 µg to 1000 µg per kilo body weight. Using multimeric forms of the compounds, the suitable dosages are often in the range of from 0.1 µg to 1000 µg per kilo body weight, such as in the range of from about 0.1 µg to 750 µg per kilo body weight, and especially in the range of from about 0.1 µg to 500 µg per kilo body weight such as in the range of from about 0.1 µg to 250 µg per kilo body weight. In particular, when administering nasally smaller dosages are used than when administering by other routes. Administration may be performed once or may be followed by subsequent administrations. The dosage will also depend on the route of administration and will vary with the age and weight of the subject to be treated. A preferred dosage of multimeric forms would be in the interval 1 mg to 70 mg per 70 kg body weight.

For some indications a localised or substantially localised application is preferred.

For another application, intranasal application is preferred.

Some of the compounds of the present invention are sufficiently active, but for some of the others, the effect will be enhanced if the preparation further comprises pharmaceutically acceptable additives and/or carriers. Such additives and carriers will be known in the art. In some cases, it will be advantageous to include a compound, which promote delivery of the active substance to its target.

In many instances, it will be necessary to administrate the formulation multiple times. Administration may be a continuous infusion, such as intraventricular infusion or administration in more doses such as more times a day, daily, more times a week, weekly, etc. It is preferred that administration of the medicament is initiated before or shortly after the individual has been subjected to the factor(s) that may lead to cell death. Preferably the medicament is administered within 8 hours from the factor onset, such as within 5 hours from the factor onset. Many of the compounds exhibit a long term effect whereby administration of the compounds may be conducted with long intervals, such as 1 week or 2 weeks.

Treatment by the use of the peptide sequences, compound(s) comprising thereof, antibodies, medicament(s) comprising thereof, and/or pharmaceutical composition(s) comprising thereof according to the invention is in one embodiment useful for modulating cell differentiation, proliferation, survival and/or motility. Accordingly, the treatment includes treatment of diseases or conditions of the muscles including conditions with impaired function of neuro-muscular connections, such as genetic or traumatic atrophic muscle disorders; or for the treatment of diseases or conditions of various organs, such as degenerative conditions of the gonads, of the pancreas, such as diabetes mellitus type I and II, of the kidney, such as nephrosis the compounds according to the invention may be used for inducing differentiation, modulating proliferation, stimulate regeneration, neuronal plasticity.

Further, the invention further concerns treatment of cancer. Regulation of proliferation, differentiation, survival and motility of cancer cells is important for growth of tumors comprising cancer cells, invasion, angiogenesis and spreading thereof. Thus, the compound may advantageously be used as a medicament for the inhibiting the later processes in cancer prophylaxis and therapy A compound, medicament and/or pharmaceutical composition of the invention may for example be used in the treatment of clinical conditions such as neoplasms such as malignant neoplasms, benign neoplasms, carcinoma in situ and neoplasms of uncertain behavior, more specifically cancer in breast, thyroidal, pancreas, brain, lung kidney, prostate, liver, heart, skin, blood organ (incl. but not limited to CML and AML), muscles, sarcoma, cancers with dysfunction and/or over- or under-expression of specific receptors and/or expression mutated receptors or associated with soluble receptors, such as but not limited to Erb-receptors ad FGF-receptors, diseases of endocrine glands, such as diabetes mellitus, pituitary gland tumor, metabolic disorders such as obscenity lipid disorders, e.g. hyper cholesterolamia, artheslerosis, diabetes type I and II, disorders of amino-acid transport and metabolism, disorders of purine and pyrimidine metabolism and gout, bone disorders, such as fracture, osteoporosis, osteo arthritis (OA), obesity, psychoses, such as senile and presenile organic psychotic conditions, alcoholic psychoses, drug psychoses, transient organic psychotic conditions, depression and other mood disorders incl. manic and bipolar disorders, Alzheimer's disease, cerebral lipidoses, epilepsy, general paresis [syphilis], hepatolenticular degeneration, Huntington's chorea, Jakob-Creutzfeldt disease, multiple sclerosis, Pick's disease of the brain, polyarteriti nodosa, syphilis, Schizophrenic disorders, affective psychoses, neurotic disorders, personality disorders, including character neurosis, nonpsychotic personality disorder associated with organic brain syndromes, paranoid personality disorder, fanatic personality, paranoid personality (disorder), paranoid traits, sexual deviations and disorders or dysfunctions including reduced sexual motivation or capability for what ever reason, sleep disorders, mental retardation, inherited or in relation with disease or trauma, disease in the nerve system and sense organs, such as affecting sight, hearing, smell, feeling, tasting, cognitive anomalies after disease, injury e.g. after trauma, surgical procedure and violence, pain syndrome such as non-opoid pain, neuropatic pain, or in pain related to other disorders e.g. diabetes, or HIV, encephalitis, drug/alcohol abuse, anxiety, postoperative nerve damage, peri-operative ischemia, inflammatory disease of the central nervous system, such as meningitis, encephalitis, cerebral degenerations such as Alzheimer's disease, Pick's disease, senile degeneration of brain, senility NOS, communicating hydrocephalus, obstructive hydrocephalus, Parkinson's disease including other extra pyramidal disease and abnormal movement disorders, spinocerebellar disease, cerebellar ataxia, Marie's, Sanger-Brown, Dyssynergia cerebellaris myoclonica, primary cerebellar degeneration, such as spinal muscular atrophy, familial, juvenile, adult spinal muscular atrophy, motor neuron disease, amyotrophic lateral sclerosis, motor neuron disease, progressive bulbar palsy, pseudobulbar palsy, primary lateral sclerosis, other anterior horn cell diseases, anterior horn cell disease, unspecified, other diseases of spinal cord, syringomyelia and syringobulbia, vascular myelopathies, acute infarction of spinal cord (embolic) (nonembolic), arterial thrombosis of spinal cord, edema of spinal cord, subacute necrotic myelopathy, subacute combined degeneration of spinal cord in diseases classified elsewhere, myelopathy, drug-induced, radiation-induced myelitis, disorders of the autonomic nervous system, disorders of peripheral autonomic, sympathetic, parasympathetic, or vegetative system, familial dysautonomia [Riley-Day syndrome], idiopathic peripheral autonomic neuropathy, carotid sinus syncope or syndrome, cervical sympathetic dystrophy or paralysis. peripheral autonomic neuropathy in disorders classified elsewhere, amyloidosis, autoimmune disorders, such as rheumatoid arthritis, SLE, ALS, and MS, anti-inflammatory effects, asthma and other allergic reactions, diseases of the peripheral nerve system, brachial plexus lesions, cervical rib syndrome, costoclavicular syndrome, scalenus anterior syndrome, thoracic outlet syndrome, brachial neuritis or radiculitis, including in newborn. Inflammatory and toxic neuropathy, including acute infective polyneuritis, Guillain-Barre syndrome, Postinfectious polyneuritis, polyneuropathy in collagen vascular disease, disorders of the globe including disorders affecting multiple structures of eye, such as purulent endophthalmitis, diseases of the ear and mastoid process, chronic rheumatic heart disease, ischaemic heart disease, arrhythmia, diseases in the pulmonary system, respiratory system, sensoring e.g. oxygen, asthma, acute myocardial infarction, and other related disorders or sequel from AMI, abnormality of organs and soft tissues in newborn, including in the nerve system, complications of the administration of anesthetic or other sedation in labor and delivery, diseases in the skin including infection, insufficient circulation problem, burn injury and other mechanic and/or physical injuries, atrophic dermatitis, psoriasis, infection caused disorders, injuries, including after surgery, crushing injury, burns. Injuries to nerves and spinal cord, including division of nerve, lesion in continuity (with or without open wound), traumatic neuroma (with or without open wound), traumatic transient paralysis (with or without open wound), accidental puncture or laceration during medical procedure, injury to optic nerve and pathways, optic nerve injury, second cranial nerve, injury to optic chiasm, injury to optic pathways, injury to visual cortex, unspecified blindness, injury to other cranial nerve(s), injury to other and unspecified nerves, poisoning by drugs, medicinal and biological substances, both acute dysfunction and chronic dysfunction e.g. deficit in cognition, mood, social functioning, after injury, peripheral and centrally, genetic or traumatic atrophic muscle disorders; or for the treatment of diseases or conditions of various organs, such as degenerative conditions of the gonads, of the pancreas, such as diabetes mellitus type I and II, of the kidney, such as nephrosis, Scrapie, Creutzfeldt-Jakob disease, Gerstmann-Straussler-Sheinker (GSS) disease, stem-cell protection or maturation in vivo or in vitro, neurogenesis.

According to invention a method of treatment and/or prevention of the above conditions and symptoms comprises a step of administering an effective amount of a peptide sequence and/or compound, and/or antibody and/or medicament, and/or pharmaceutical composition of the invention to an individual in need.

6. Examples

```
Peptides:
Inherbin group
Full length peptides:
Inherbin 1        MLYNPTTYQMDVNPEGK    SEQ ID NO: 1

Inherbin 2        VTYNTDTFESMPNPEGR    SEQ ID NO: 2

Inherbin 3        LVYNKLTFQLEPNPHTK    SEQ ID NO: 3

Inherbin 4        FVYNPTTFQLEMNFNAK    SEQ ID NO: 4

Mouse ErbB2dl     ITYNTDTFESMLNPEGR    SEQ ID NO: 5

Mouse ErbB3dl:    LVYNKLTFQLEPNPHIK    SEQ ID NO: 6

Truncated peptides:
B1dln             LMLYNPTT             SEQ ID NO: 30

B1dlc             TYQMDVN              SEQ ID NO: 31

B2dln             LVTYNTD              SEQ ID NO: 32

Mouse B2dln       LITYNTD              SEQ ID NO: 33

B2dlc             TFESMPN              SEQ ID NO: 34

Mouse B2dlc       TFESMLN              SEQ ID NO: 35

B3dln             PLVYNKLT             SEQ ID NO: 36

B3dlc             TFQLEPN              SEQ ID NO: 37

B4dln             TFVYNPT              SEQ ID NO: 38

B4dlc             TFQLEMN              SEQ ID NO: 39

Scrambled peptide:
Scr-Inherbin3d    KHKLPYNFNLETTVQPL    SEQ ID NO: 40

Autoinhibitory loop group:
AUER1c            AGVMGENNTL           SEQ ID NO: 7

Mouse AUER1c      AGIMGENNTL           SEQ IS NO: 8

AUER1n            AHYIDGPHSVKT         SEQ ID NO: 9

AUER2c            SGVKPDLSYM           SEQ ID NO: 10

AUER2n            AHYKDPPFSVAR         SEQ ID NO: 11

Mouse AUER2n      AHYKDSSSCVAR         SEQ ID NO: 12

AUER3c            HGVLGAKGPI           SEQ ID NO: 13

Mouse AUER3c      HGILGAKGPI           SEQ ID NO: 14

AUER3n            AHFRDGPHSVSS         SEQ ID NO: 15

Mouse AUER3n      AHFRDGPHCVNS         SEQ ID NO: 16

AUER4c            DGLQGANSFI           SEQ ID NO: 17

AUER4n            SHFKDGPNSVEK         SEQ ID NO: 18

Membrane proximal group:
InhB2_1           GLPREYVNARHCL        SEQ ID NO: 19

Mouse InhB2_1     GLPREYVRGKHCL        SEQ ID NO: 20

InhB2_2           HPECQPQNGSVT         SEQ ID NO: 21

Mouse InhB2_2     HPECQPQNSSET         SEQ ID NO: 22

InhB2_3           FGPEADQCVA           SEQ ID NO: 23

Mouse InhB2_3     YGSEADQCEA           SEQ ID NO: 24

InhB2_4           HYKDPPFCVAR          SEQ ID NO: 25

Mouse InhB2_4     HYKDSSSCVAR          SEQ ID NO: 26

InhB2_5           SGVKPDLS             SEQ ID NO: 27

InhB2_6           YMPIWKFPDEEGA        SEQ ID NO: 28

Mouse InhB2_6     YMPIWKYPDEEGI        SEQ ID NO: 29
```

Methods:

Peptides

The Inherbin3 peptide (SEQ ID NO:3) was synthesized in two forms: a) as a monomeric linear peptide, and b) as a tetrameric dendrimer, termed Inherbin3d, composed of four monomers coupled to a lysine backbone. The Inherbin1 (SEQ ID NO:1), Inherbin2 (SEQ ID NO:2), and Inherbin4 (SEQ ID NO:4) peptides were only synthesized as tetrameric dendrimers used for binding analysis. The scrambled Inherbin3 peptide (SEQ ID NO:40) was only synthesized in the dendrimeric form, and termed Scr-Inherbin3d. The dendrimeric peptides were purified by dialysis of peptide dissolved in distilled water against pure distilled water in a 1 kDa cut-off dialysis tube (Millipore, Billerica, Mass., USA). The monomeric peptides were of high purity upon synthesis, not needing further purification.

Surface Plasmon Resonance Analysis

Binding analyses were performed with the surface plasmon resonance (SPR)-based biosensor instrument BIAcore2000 (BIAcore AB, Uppsala, Sweden), at 25° C. using ready-made HBS-EP buffer (BIAcore AB) as running buffer. Peptides were immobilized on the surface of a CM5 sensor chip (BIAcore AB) using an amine coupling kit (Biosensor AB, Uppsala, Sweden) according to the manufacturer's instructions, at a flow rate of 5 µl/min. Briefly, carboxyl groups on the sensor chip surface were activated by injection of 35 µl activation solution followed by injection of peptide (50 µg/ml peptide in HBS-EP buffer, pH 7.4) until the desired level of immobilized peptide was reached. Unreacted peptide was washed out and unreacted activated groups were blocked by the injection of 35 µl 1 M ethanolamine. The final immobilization response was app. 7000-9000 resonance units (RU). A reference surface was generated simultaneously under the same conditions but without peptide injection and used as a blank chip control. ErbB receptor proteins were injected at various concentrations at a flow rate of 20 µl/min, and binding to the peptides immobilized on the chip was measured in real-time. The curve corresponding to the difference between signals on flow cells with immobilized peptide and the signal on the blank flow cell was used for analysis. Each sensorgram consists of an association phase (the first 320 seconds), reflecting binding of the injected receptor to the peptide, and a dissociation phase (app. 300 seconds), during which running buffer is passed over the chip and the bound receptor is being washed off. Data were analyzed by nonlinear curve fitting using the manufacturer' software. The recombinant protein comprising the whole extracellular part of human ErbB1 (also termed the EGF receptor, EGFR) was purchased from Research Diagnostics (Concord, Mass., USA). Recombinant proteins comprising the Fc region of human IgG$_1$ and the Fc protein fused to the extracellular parts of human ErbB2, ErbB3 or ErbB4 were purchased from R&D Systems Europe (Abingdon, UK).

ErbB Receptor Phosphorylation

The cells employed for this assay were NR6 wtEGFR cells, which are fibroblastoid cells stably transfected with ErbB1, and human head and neck tumor-derived HN5 cell. Confluent NR6 wtEGFR or HN5 cells were treated with peptide in the indicated concentrations for 30 min, then stimulated with 10 ng/ml EGF (Sigma-Aldrich, St. Louis, Mo., USA) for 10 min. Cells were lysed in lysis buffer (1% (v/v) Triton X-100, 150 mM NaCl, 10 mM Tris pH 7.4, 1 mM EDTA, 1 mM EGTA, 0.5% (v/v) NP-40, phosphatase inhibitors (Phosphatase Inhibitor Cocktail Set II from Calbiochem, La Jolla, Calif., USA) and protease inhibitors (Complete™ Protease Inhibitor Cocktail from Boehringer Mannheim Biochemica, Mannheim, Germany)), and cleared lysate samples containing equal amounts of total protein (as determined by a bicinchoninic acid assay (Pierce, Rockford, Ill., USA)) were subjected in duplicates to 4-12% SDS-PAGE and immunoblotting. One membrane was probed with anti-phospho-EGFR (phosphotyrosine 1068) antibody (Cell Signaling Technology, Danvers, Mass., USA), the other with anti-EGFR antibody (Cell Signaling Technology). Detection was carried out using horseradish peroxidase (HRP)-conjugated secondary antibodies (DAKO, Denmark) and enhanced chemiluminiscence (Pierce). The intensity of bands was quantified using densitometric analysis employing the software package GeneTools (Syngene, Cambridge, UK).

Cell Proliferation (BrdU Incorporation):

2000 L929 cells (ECACC no: 85011425) per well were seeded in a 96 well plate in full medium (containing 10% foetal calf serum) or starvation medium (serum-free). Peptides, ErbB1 kinase inhibitor PD153035 (Calbiochem), and EGF (Sigma-Aldrich) were added immediately after seeding of the cells (for experiments done in full serum) or after 8 hours of incubation (for experiments done in starvation medium) in the concentrations indicated in figures. Cells were grown for 6 hours, then 10 µM bromodeoxyuridine (BrdU) was added, and cells were grown for additional 18 hours. Then, BrdU incorporation in the cells was assayed using the Biotrak ELISA System, version 2 from Amersham Biosciences Europe GmbH (Buckinghamshire, UK) following the manufacturer's protocol.

Cell Viability (MTS Staining):

2000 HN5 cells per well were seeded in a 96 well plate in full medium (containing 10% fetal calf serum) or starvation medium (serum-free). After 12 hours of incubation, peptides or ErbB1 kinase inhibitor PD153035 (Calbiochem) and/or EGF (Sigma-Aldrich) were added in the concentrations indicated in figures. Cells were grown for 72 hours, then 20 µl MTS One Solution Reagent (Promega, Madison, Wis., USA) were added per 100 µl culture medium in each well, and the plates were incubated for 1-2 hours at 37° C., followed by absorbance measurements at 490 nm.

Cell Motility Assay:

Subconfluent L929 cells were infected with Ad5.CMV-GFP virus according to the manufacturer instruction (Clontech). 24 h after transfection, cells were seeded at a density of $4 \times 10^3$ cells/cm$^2$ and grown for 24 h. Cells were then treated with the indicated concentration of peptide and EGF, and cell positions were recorded every 15 min at 25 fixed positions in each culture for 4 hours using automatic time-lapse video recording. The workstation employed comprised an Eclipse TE300 inverted microscope (Nikon, Japan) equipped with a heated, movable, computer controlled microscope stage. Recordings were performed using the PRIGRA software (developed at the Protein Laboratory, Copenhagen, Denmark).

Analysis of individual cell motility was performed using an automatic procedure for single cell motility evaluation. Briefly, automatic marking of cell positions in consecutive video frames was used for determination of the migration tracks of the cells during the whole recording period. The obtained cell coordinate data were used for the calculation of motility parameters by means of the 'complex overlapping' method. Briefly, the mean squared cell displacement, $\langle d^2 \rangle$, was calculated as the Euclidean distance between two points corresponding to the initial and final position of the cell. The rate of diffusion, R, was calculated by fitting the curve of $\langle d^2 \rangle$ plotted against time to the equation $$\langle d^2(t_i) \rangle = R(\tau - P(1 - e^{(-\tau/P)})),$$

where $t_i$ is the time interval of interest, $\tau$ is the time interval between observations, i.e. 15 min, and P is the persistence time in direction (28). The mean cell speed, $S_\tau$, was calculated as the mean cell displacement taking place between discrete observations ($\langle d_\tau \rangle$) divided by the time interval between discrete observations ($\tau$), according to the equation:

$$\langle S_\tau \rangle = \frac{\langle d_\tau \rangle}{\tau}$$

The mean cell-path-length, $\langle L \rangle$, for a sample of a population of cells at a given time of observation, was calculated as:

$$L = \frac{1}{N} \sum_{k=1}^{N} \sum_{s=1}^{t_{obs}} \sqrt{(x_k(t_s) - x_k(t_{s-1}))^2 + (y_k(t_s) - y_k(t_{s-1}))^2}$$

The locomotive index, LI, was calculated as the ratio of the mean cell displacement and the mean cell-path-length:

$$LI = \frac{\langle d \rangle}{\langle L \rangle}$$

LI was used as a measure of the directional persistence of the cells.

ErbB Receptor Phosphorylation Assay:

NR6 wtEGFR cells (a fibroblastoid cell line stably transfected with ErbB1) were treated with peptide in the indicated concentrations for 1 hour, then stimulated with 10 ng/ml EGF for 10 min. Cells were lysed in lysis buffer (1% (v/v) Triton X-100, 150 mM NaCl, 10 mM Tris pH 7.4, 1 mM EDTA, 1 mM EGTA, 0.5% (v/v) NP-40, phosphatase inhibitors, and protease inhibitors), and cleared lysate samples containing equal amounts of total protein (as determined by a bicinchoninic acid assay (Pierce, Ill., USA)) were subjected in duplicates to 4-12% SDS-PAGE and immunoblotting. One membrane was probed with anti-phospho-ErbB1 (tyrosine 1068) antibody, the other with anti-ErbB1 antibody. Detection was carried out using horseradish peroxidase conjugated secondary antibodies and enhanced chemiluminiscence (Pierce). The intensity of bands was quantified using densitometric analysis employing the software package GeneTools (Syngene, Cambridge, UK).

Results:

Binding of Inherbin Peptides to ErbB Receptors

The binding of three Inherbin peptides to all four members of the ErbB receptor family was determined using surface plasmon resonance (SPR) binding analysis (table 1). Data represents mean $K_D$ values±SEM. We found that each of the peptides Inherbin1, Inherbin3, and Inherbin4 bound to several members of the ErbB receptor family, but with different specificities. FIG. 1 shows representative binding curves for the binding of the Inherbin3 peptide to the extracellular parts of ErbB1-4 produced as recombinant monomeric (ErbB1) or dimeric Fc chimeric proteins (ErbB2-4) as well as to a control protein consisting only of the Fc part of human IgG.

TABLE 1

$K_D$ values for the binding of Inherbin peptides to ErbB receptors as determined by SPR analysis

|  | 1DL | 2DL | 3DL | 4DL |
| --- | --- | --- | --- | --- |
| ErbB1 | 1.36e−8 ± 4.9e−9 | Not tested | 7e−8 ± 2.8e−8 | 2.97e−7 ± 1.4e−7 |
| ErbB2 | No binding |  | No binding | 4.3e−8 ± 1.5e−8 |
| ErbB3 | 4.9e−8 ± 8e−9 |  | 1.79e−8 ± 3.8e−9 | 1.99e−8 ± 5.9e−9 |
| ErbB4 | No binding |  | No binding | 9.04e−8 ± 3.5e−8 |

Figure 2:
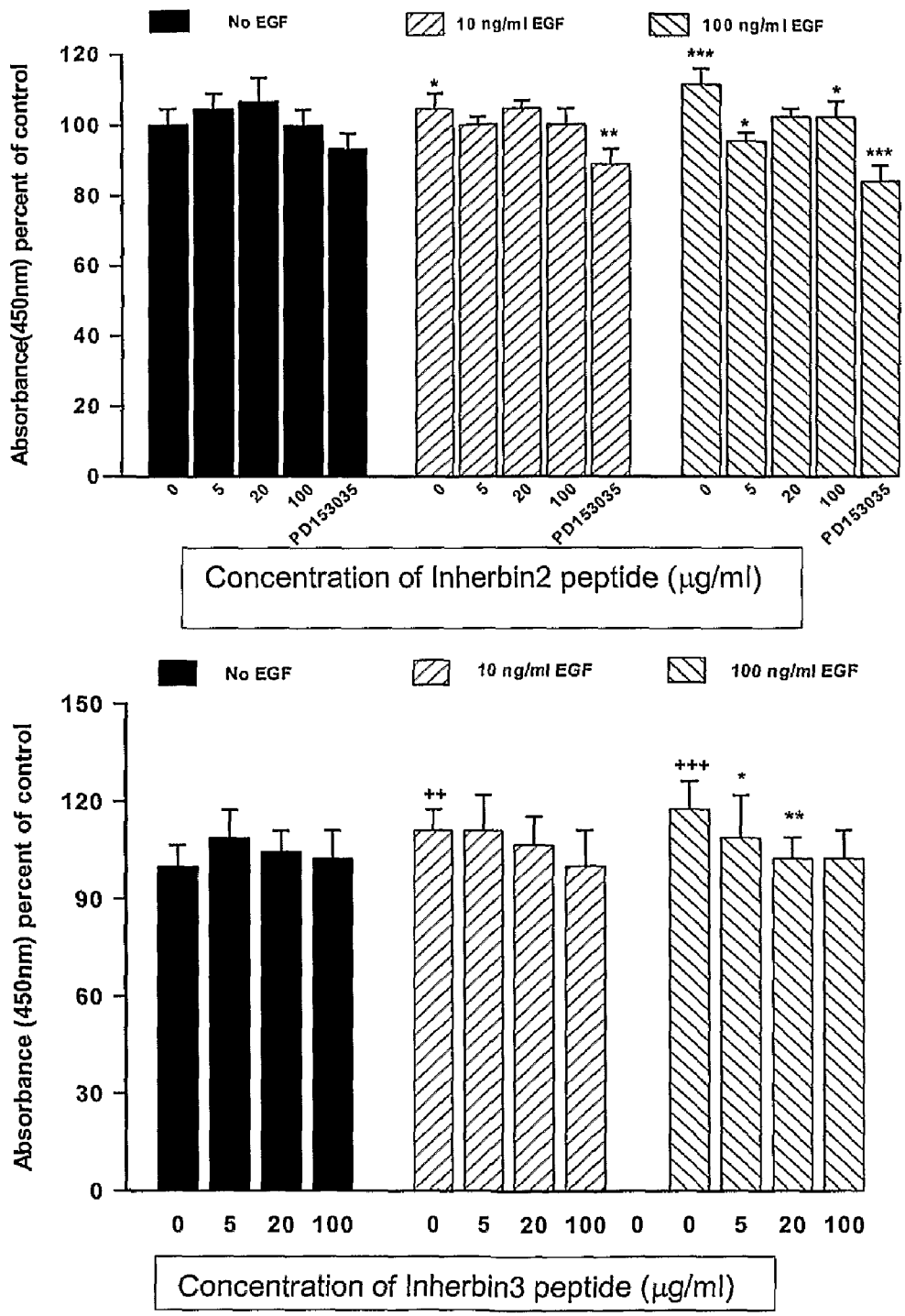
FIG. 2: Effect of Inherbin2 and Inherbin3 on L cell proliferation. L929 cells were seeded in full medium, and treated with the indicated doses of Inherbin2 (A) or Inherbin3 (B) and EGF for 6 hours, then BrdU was added to the cells, and they were incubated for additionally 18 hours (still in the presence of Inherbin3 and EGF) before BrdU incorporation was determined by means of an ELISA-based assay. Data represents means±SEM for 6 independent experiments. Crosses indicate significant difference as compared to unstimulated cells not treated with peptide (no EGF, no peptide), and stars indicate significant difference as compared to cells stimulated with the same dose of EGF but not treated with peptide. + and *=$p<0.05$, **=$p<0.02$, +++=$p<0.001$, as determined by repeated measurements ANOVA followed by Dunnett's post-test.

The Inherbin2 and Inherbin3 Peptides Inhibits EGF-Induced Proliferation in L929 Fibroblasts To test the ability of the Inherbin peptides to inhibit ErbB-mediated cell proliferation, we tested the effect of the Inherbin2 and Inherbin3 peptides on EGF-induced cell proliferation in L929 cells (FIG. 2). We found that both peptides were able to inhibit EGF-induced cell proliferation significantly.

Figure 3:
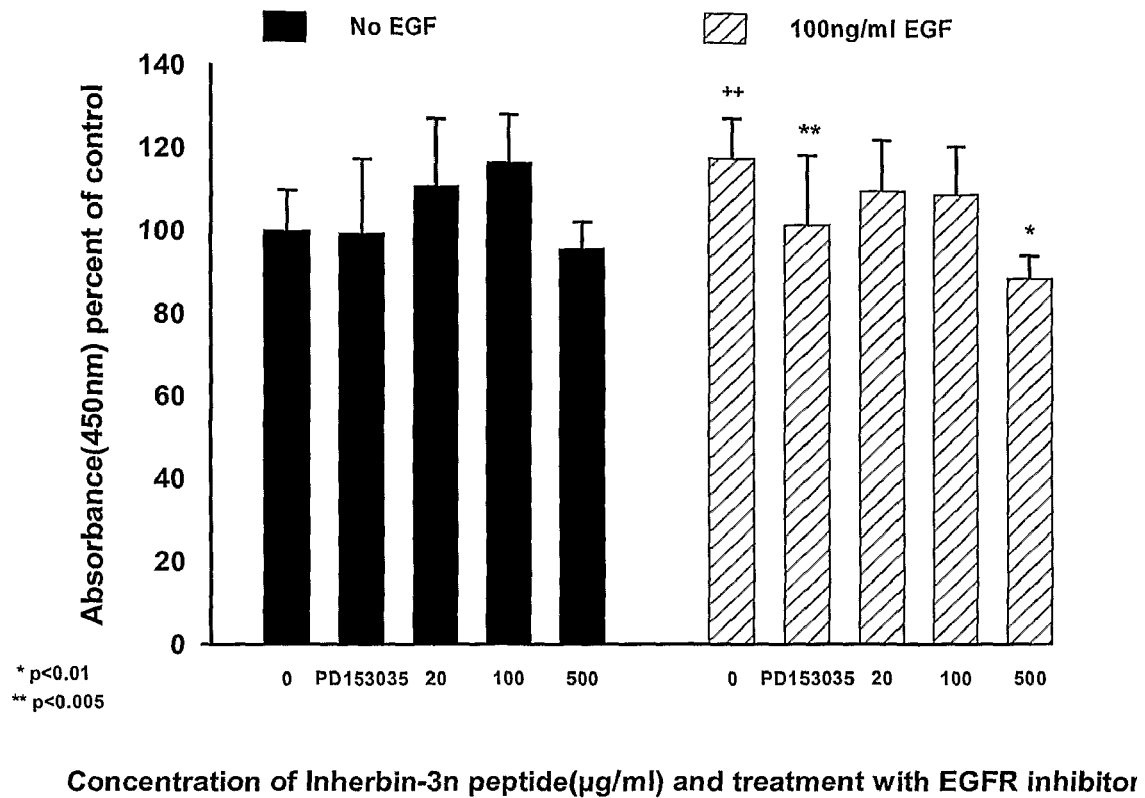
FIG. 3: Effect of a truncated version of Inherbin3 (termed Inherbin3n) on L cell proliferation. L929 cells were seeded in full medium, and treated with the indicated doses of Inherbin3n, the pharmacological ErbB1 inhibitor PD153035, and EGF for 6 hours, then BrdU was added to the cells, and they were incubated for additionally 18 hours (still in the presence of Inherbin3 and EGF) before BrdU incorporation was determined by means of an ELISA-based assay. Data represents means±SEM for 6 independent experiments. Crosses indicate significant difference as compared to unstimulated cells not treated with Inherbin3n (no EGF, no Inherbin3n), and stars indicate significant difference as compared to cells stimulated with the same dose of EGF but not treated with Inherbin3n. + and *=$p<0.05$, **=$p<0.02$, +++=$p<0.001$, as determined by repeated measurements ANOVA followed by Dunnett's post-test.

A Truncated Version of Inherbin3 (Termed Inherbin3n) Inhibits EGF-Induced Proliferation in L929 Fibroblasts A truncated peptide, constituting the N-terminal half of the Inherbin3 peptide was produced, and termed Inherbin3n. To compare the biological effect of this peptide to the effect of Inherbin3, the effect of Inherbin3n on EGF-induced L cell proliferation was determined (FIG. 3). We found that the Inherbin3n peptide inhibited EGF-induced cell proliferation to the same extent as Inherbin3.

The Dendrimeric Inherbin3d Peptide is a More Potent Inhibitor of EGF-Induced Cell Proliferation in L Cells than Monomeric Inherbin3.

Figure 4:
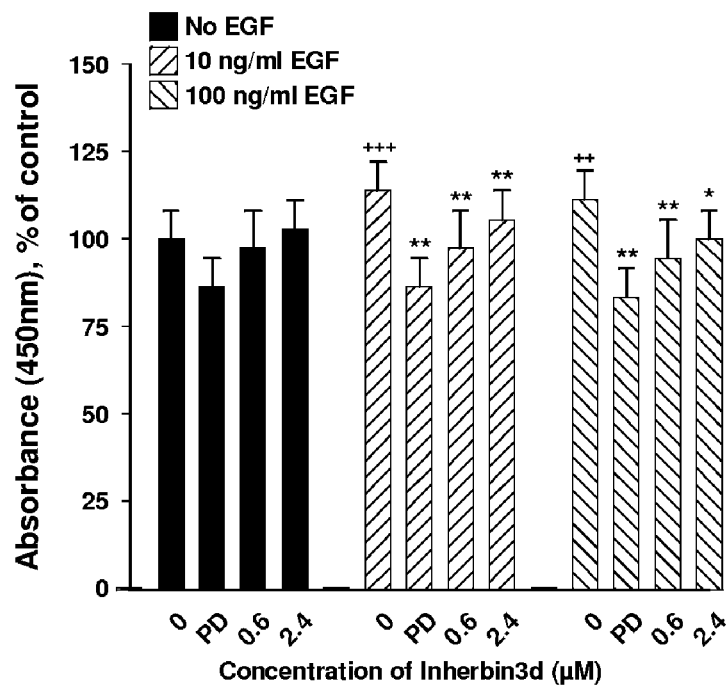
FIG. 4: Effect of Inherbin3d on L cell proliferation. L929 cells were seeded in starvation medium, and treated with the indicated doses of Inherbin3d, and EGF and/or 100 nM PD153035 for 6 hours, then BrdU was added to the cells, and they were incubated for additionally 18 hours (still in the presence of Inherbin3d and EGF) before BrdU incorporation was determined by means of an ELISA-based assay. Data represent means±SEM for 7 independent experiments. Crosses indicate significant difference as compared to unstimulated cells not treated with Inherbin3d (no EGF, no Inherbin3d), and stars indicate significant difference as compared to cells stimulated with the same dose of EGF but not treated with Inherbin3d. *=$p<0.05$, ++ and **=$p<0.02$, +++=$p<0.001$, as determined by repeated measurements ANOVA followed by Dunnett's post-test.

The Inherbin3 peptide was synthesised in two versions: a monomeric linear peptide (used in the above presented biological assays) and a tetrameric dendrimer (used for the binding analysis). In order to compare the potencies by which the two versions of Inherbin3 induce their biological effects, we examined the effect of the dendrimeric Inherbin3d peptide on proliferation of L929 cells. We found that dendrimeric Inherbin3d, as was the case for monomeric Inherbin3, inhibited EGF-induced cell proliferation (FIG. 4). However, whereas monomeric Inherbin3 only significantly inhibited cell proliferation induced by 100 ng/ml EGF, and only in peptide doses of 2.5 μM and 10 μM (see FIG. 2), dendrimeric Inherbin3d significantly inhibited cell proliferation induced by either 10 or 100 ng/ml EGF in peptide doses as low as 0.6 μM (FIG. 4). We also examined the effect of the specific ErbB1 tyrosine kinase inhibitor PD153035 on cell proliferation, and found that this inhibitor blocked cell proliferation induced by stimulation with either 10 or 100 ng/ml EGF (FIG. 4). From these data we conclude that dendrimeric Inherbin3d is a more potent inhibitor of EGF-induced L929 cell proliferation than monomeric Inherbin3, and that the inhibitory effect of Inherbin3d in these cells is comparable to the effect of PD153035.

Figure 5:
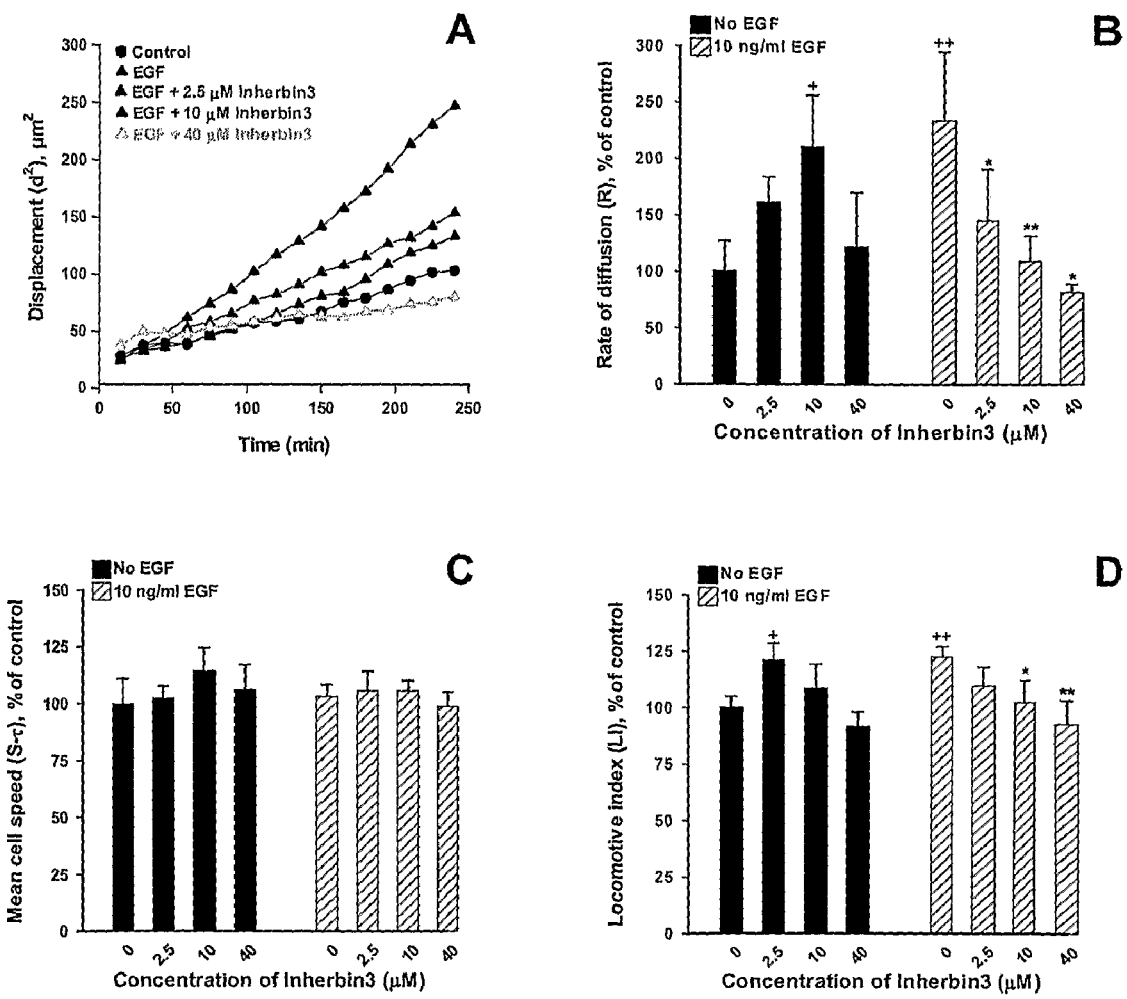
FIG. 5: Effect of Inherbin3 on cell motility. L929 cells infected with adenovirus encoding EGFP were stimulated with the indicated doses of EGF and Inherbin3, and cell motility was recorded for 4 hours using automatic time-lapse video recording. A, Plots of mean squared cell displacement ($d^2$) against time for one representative experiment, showing the effect of Inherbin3 on EGF-induced cell motility. B, C and D shows the rate of diffusion, R (B), mean cell speed, $S_\tau$ (C) and locomotive index, LI (D) calculated as described in Materials and Methods. The data are presented means±SEM for 6 independent experiments, and values for untreated cells (no EGF, no Inherbin3) are set to 100%. Stars represent significant differences as compared to cells not treated with Inherbin3 but stimulated with EGF (i.e. data in column 5). Crosses represent significant differences as compared to untreated (no EGF, no Inherbin3) cells. + and *=$p<0.05$, ++ and **=$p<0.02$, as determined by repeated measurements ANOVA followed by Dunnett's post-test.

Inherbin3 Inhibits EGF-Induced Cell Motility and Stimulates Basal Cell Motility in the Absence of EGF Motility of L929 cells infected with an adenovirus construct encoding an enhanced version of the green fluorescent protein, EGFP, was determined by means of an automatic evaluation system that recognises coordinates of green cells on consecutive video frames in order to generate cell tracks (Dmitryev et al., 2006). The results of the cell motility determinations are shown in FIG. 5. The average rate of cell diffusion, termed R, was stimulated strongly by EGF, and this EGF-induced increase in rate of diffusion was significantly inhibited by the Inherbin3 peptide (FIG. 5B). In a dose of 40 μM Inherbin3 completely blocked the EGF-induced increase in rate of diffusion (FIG. 5B). This effect of Inherbin3 on EGF-induced cell motility is also illustrated in FIG. 5A that shows the mean squared cell displacement ($d^2$) plotted against time for untreated cells and cells treated with EGF with and without concomitant treatment with Inherbin3 for one representative experiment. Apart from its inhibitory effect on EGF-induced cell motility, we found that Inherbin3 itself (in the absence of EGF) in a dose of 10 μM stimulated the rate of diffusion to the level of the EGF-induced response (FIG. 5B).

To explore further the changes in the rate of cell diffusion induced by EGF and Inherbin3, we determined the mean cell speed, $S_r$, and the locomotive index, LI, for all experimental conditions. As can be seen in FIGS. 5C and 5D either EGF or Inherbin3 did not significantly affect the mean cell speed, whereas the locomotive index reflected the changes seen in rate of diffusion. This indicates that the EGF- and Inherbin3-induced changes in rate of diffusion are not due to changes in mean cell speed, but rather changes in the directional persistence of the cells, as reflected by the locomotive index.

In conclusion, the data in FIG. 5 show that Inherbin3 dose-dependently inhibits EGF-induced cell motility. Furthermore, Inherbin3 in itself has a stimulatory effect on cell motility in the absence of EGF.

Figure 6:
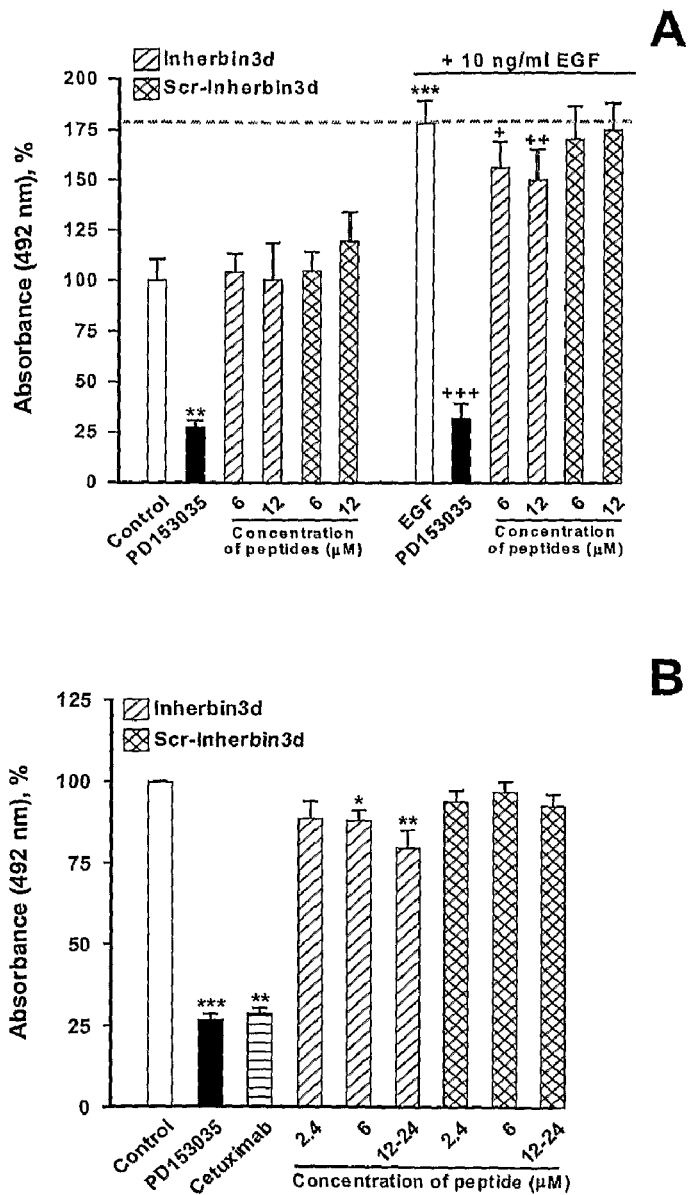
FIG. 6: Effect of Inherbin3d on growth of ErbB1 overexpressing head and neck cancer cells. A, HN5 cells were seeded in starvation medium, grown for 12 hours, after which the indicated doses of Inherbin3d and Scr-Inherbin3d, 10 ng/ml EGF and/or 100 nM PD153035 was added to the cells. Cells were then incubated for 3 days, and cell growth was measured with MTS staining. B, HN5 cells were seeded in full medium (containing 10% fetal calf serum) and treated with the indicated doses of Inherbin3d and Scr-Inherbin3d, or 100 nM PD153035. Cells were grown for 3 days and cell growth was measured with MTS staining. Data represents means±SEM for 6-8 independent experiments. Stars indicate significant differences as compared to untreated cells (control), and crosses indicate significant differences as compared to cells stimulated with EGF but not treated with peptides or PD153035. + and *=$p<0.05$, ++ and =$p<0.02$, +++ and *=$p<0.001$, as determined by repeated measurements ANOVA followed by Dunnett's post-test.

Inherbin3 Inhibits Growth of Human ErbB1 Overexpressing Head and Neck Cancer Cells To evaluate the effect of Inherbin3 in cells overexpressing ErbB1 at a high level we determined the effect of Inherbin3d (the dendrimeric version) on EGF-induced and serum-induced growth of the ErbB1 overexpressing human head and neck cancer cell line HN5, which has been shown to express ErbB1 at a level of app. $5.2 \times 10^6$ receptors per cell (Kwok and Sutherland 1991). The results are shown in FIG. 6. Firstly, we found that when starved cells were stimulated with EGF, the cells responded with a strong increase in cell growth, and concomitant treatment with Inherbin3 inhibited this EGF-induced cell growth response. However, the effect of Inherbin3 in these cells was relatively low (app. 35% inhibition of the EGF-induced increase in cell growth) compared to the earlier described effects on EGF-induced cell proliferation, cell motility, and ErbB1 phosphorylation in cells with a lower ErbB1 expression level (in these cells, treatment with Inherbin3 gave almost 100% inhibition of the EGF-induced effects). Thus, we conclude that the effect of Inherbin3 on EGF-induced ErbB1 function depends on the expression level of ErbB1. Inherbin3 had no effect on the basal cell growth (without EGF-stimulation) under these conditions (FIG. 6A), which is in accordance with the effect of Inherbin3 on L929 cell proliferation. Secondly, we found that when cells were grown in full medium (containing 10% serum), Inherbin3 inhibited serum-induced cell growth (FIG. 6B). However, the effect of Inherbin3 on serum-induced cell growth was relatively weak, similarly to the effect of the peptide on EGF-induced cell growth, again suggesting a weak effect of Inherbin3 on cells with strong ErbB1 overexpression. We also tested the effect of PD153035 on HN5 cell growth, and found that this ErbB1 kinase inhibitor strongly inhibited growth of the cells both in absence and presence of EGF-stimulation and in the absence and presence of serum (FIGS. 6A and B).

A Scrambled Version of Inherbin3 has No Effect on the Growth of HN5 Cells

In order to address the specificity of the observed effects of Inherbin3, we designed a control peptide with the same amino acid composition as Inherbin3, but in a randomly scrambled sequence. This scrambled control peptide was synthesized as a tetrameric dendrimer, termed Scr-Inherbin3d, and the effect of this peptide on HN5 cell growth was compared with the effect of Inherbin3d. As seen in FIGS. 6A and B, the scrambled peptide had no significant effects on HN5 cell growth either in the absence or presence of EGF and either in the absence or presence of serum.

In conclusion, our data from the HN5 cells indicate that Inherbin3 can inhibit EGF-induced as well as serum-induced HN5 cell growth, although this inhibition is weaker than the inhibitory effects of the peptide observed in cells with a low or moderate ErbB1 expression level. Furthermore, we show that these effects are specific for the Inherbin3 amino acid sequence, since a scrambled control peptide did not exert these effects. Finally, we show that Inherbin3 is a less potent inhibitor of EGF-induced and serum-induced HN5 cell growth than the ErbB1 kinase inhibitor PD153035.

Figure 7:
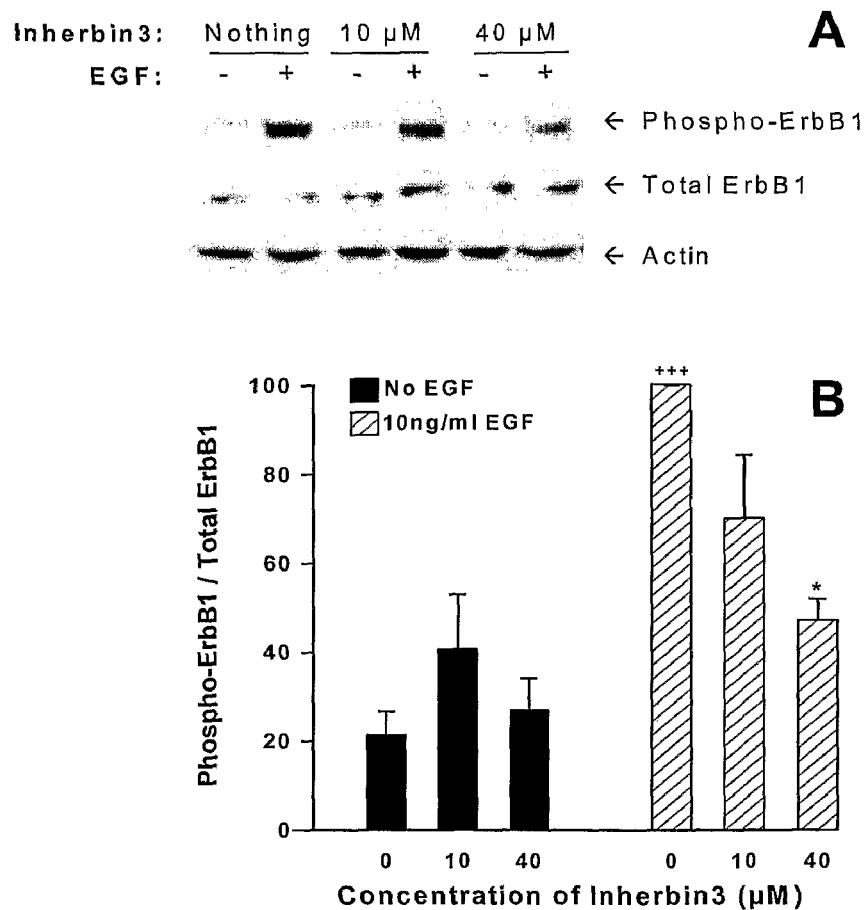
FIG. 7: Dose-dependent effect of Inherbin3 on ErbB phosphorylation. NR6 wtEGFR cells were treated with the indicated doses of Inherbin3 for 30 min followed by stimulation with 10 ng/ml EGF for 10 min. Cell lysates were subjected to immunoblotting against phosphorylated ErbB1, followed by membrane stripping and reprobing against total ErbB1 and actin. A, Representative blots from one experiment, B, Densitometric quantifications of phospho-ErbB1 and total-ErbB1 immunoblots from seven independent experiments. The level of ErbB1 phosphorylation is given as means±SEMs of ratios between the intensities of bands in phospho-ErbB1 blots and intensities of the corresponding bands in total-ErbB1 blots. The level of ErbB1 phosphorylation in EGF-treated cells not treated with peptide is set as 100%. +++ indicates $p<0.001$ as compared to the level of ErbB1 phosphorylation in untreated (no peptide, no EGF) cells, * indicates $p<0.05$ as compared to EGF-stimulated cells not treated with peptide. Statistical analysis was done by the student's paired t-test.
Figure 8:
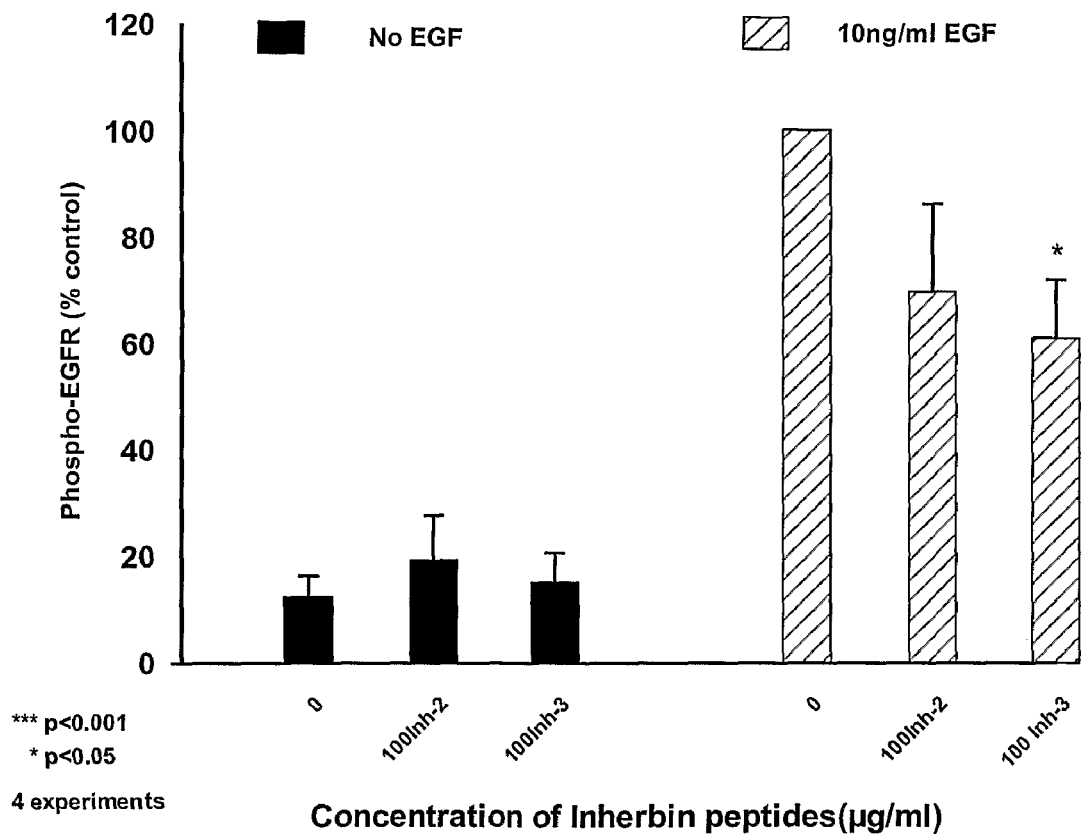
FIG. 8: Effect of Inherbin 2 and Inherbin 3 on ErbB phosphorylation. HN5 cells were treated with 100 µM of Inherbin 2 or Inherbin 3 for 30 min followed by stimulation with 10 ng/ml EGF for 10 min. Cell lysates were subjected to immunoblotting against phosphorylated ErbB1. Densitometric quantifications of phospho-ErbB1 immunoblots were obtained from four independent experiments. The level of ErbB1 phosphorylation, expressed as a percentage of control phospho-ErbB1 level, is given as mean±SEM. The level of ErbB1 phosphorylation in 10 nM EGF-treated cells not treated with either Inherbin 2 or Inherbin 3 peptide was set as 100%. * indicates $p<0.05$ as compared to EGF-stimulated cells not treated with either peptide. Statistical analysis was done by the student's paired t-test.

The Inherbin3 Peptide Inhibits EGF-Induced ErbB1 Phosphorylation in Two Different ErbB1 Overexpressing Cell Lines:

To test the ability of the Inherbin3 peptide to inhibit ErbB1 activity, we determined the effect of Inherbin3 on ErbB1 phosphorylation in a cell line stably transfected with ErbB1 and with very low expression level of ErbB2-4 termed NR6 wtEGFR (FIG. 7). We found that Inherbin3 inhibited EGF-induced ErbB1 phosphorylation significantly. We also tested the effect of Inherbin2 and Inherbin3 on EGF-induced ErbB1 phosphorylation in the HN5 cell line (FIG. 8). Here, we found that Inherbin3 significantly inhibited EGF-induced ErbB1 phosphorylation, whereas the effect of Inherbin2 was not statistically significant.

The invention claimed is:

1. An isolated peptide consisting of the amino acid sequence of SEQ ID NO:3 or a fragment or variant of SEQ ID NO:3 having at least 60% homology to SEQ ID NO:3 and a length of at least 40% and at most 100% of SEQ ID NO:3, wherein said peptide binds to and modulates the activity of an ErbB receptor selected from ErbB1, ErbB2, ErbB3, and ErbB4.

2. The peptide of claim 1 which is a variant of SEQ ID NO:3, wherein said variant has at least 90% homology to SEQ ID NO:3.

3. The peptide according to claim 1, wherein said peptide binds to the ErbB receptor with a binding affinity (Kd) of between $10^{-6}$M and $10^{-9}$M.

4. A compound comprising two or more peptides according to claim 1, wherein said peptides are linked via a peptide bond or a linker group.

5. The peptide according to claim 1, wherein said peptide modulates cell motility, proliferation, differentiation and/or survival.

6. The compound according to claim 4, wherein said compound stimulates cell motility.

7. The compound according to claim 4, wherein said compound inhibits cell motility.

8. The compound according to claim 4, wherein said compound stimulates cell proliferation.

9. The compound according to claim 4, wherein said compound inhibits cell proliferation.

10. The compound according to claim 4, wherein said compound stimulates cell differentiation.

11. A compound consisting of a peptide according to claim 1, wherein one or more amino acids of said peptide comprise a modification selected from the group consisting of amidation, glycosylation, acetylation, and phosphorylation.

12. The compound of claim 4, wherein said peptides are formulated as a dendrimer comprising four or more identical peptides.

13. The compound of claim 4 comprising two identical peptides.

14. The compound of claim 4 comprising two non-identical peptides.

15. A medicament comprising a peptide according to claim 1 or a compound according to claim 4.

16. A pharmaceutical composition comprising a medicament according to claim 15.

17. The compound according to claim 4, wherein the compound comprises a dimer or a tetramer of the peptide.

18. An isolated peptide consisting of the amino acid sequence of SEQ ID NO:6.

* * * * *